United States Patent

Krämer et al.

Patent Number: 5,094,681
Date of Patent: Mar. 10, 1992

[54] HERBICIDAL 5H-FURAN-2-ONE DERIVATIVES

[75] Inventors: Wolfgang Krämer, Burscheid; Gerd Kleefeld, Duesseldorf; Jürgen Bachmann, Leverkusen; Peter Babczinski, Wuppertal; Hans-Joachim Santel, Leverkusen; Klaus Lürssen; Robert R. Schmidt, both of Bergisch Gladbach, all of Fed. Rep. of Germany

[73] Assignee: Bayer Aktiengesellschaft, Leverkusen, Fed. Rep. of Germany

[21] Appl. No.: 575,517

[22] Filed: Aug. 30, 1990

[30] Foreign Application Priority Data

Sep. 23, 1989 [DE] Fed. Rep. of Germany ....... 3931773
May 5, 1990 [DE] Fed. Rep. of Germany ....... 4014420

[51] Int. Cl.$^5$ .............. A01N 43/08; A01N 43/36; C07D 307/58
[52] U.S. Cl. .................................. 71/88; 71/94; 71/95; 549/313; 549/318; 549/321; 548/517; 546/207
[58] Field of Search .............. 549/313, 321, 318; 71/88, 94, 95; 546/207; 548/517

[56] References Cited

U.S. PATENT DOCUMENTS

| | | | |
|---|---|---|---|
| Re. 27,894 | 1/1974 | Gerike et al. | 549/321 |
| 4,539,332 | 9/1985 | Biftu et al. | 548/517 |
| 4,568,376 | 2/1986 | Ward | 71/94 |
| 4,568,377 | 2/1986 | Ward | 71/94 |
| 4,606,756 | 8/1986 | Ward | 71/94 |
| 4,643,758 | 2/1987 | Buron, Jr. et al. | 71/95 |
| 4,774,334 | 9/1988 | Georgiev et al. | 548/517 |
| 4,797,417 | 1/1989 | Okamoto et al. | 549/313 |
| 4,916,241 | 4/1990 | Hayward et al. | 549/313 |
| 4,957,917 | 9/1990 | Lee | 549/313 |

FOREIGN PATENT DOCUMENTS

| | | |
|---|---|---|
| 0299694 | 1/1989 | European Pat. Off. |
| 2164677 | 7/1987 | Japan ................ 549/313 |
| 0174983 | 7/1988 | Japan ................ 549/321 |

OTHER PUBLICATIONS

Tetrahedron Letters, vol. 29, No. 17, pp. 2085-2088, 1988.
Can. J. Chem., vol. 64, 1986, pp. 104-109.
J. Chem. Soc. Perkin Trans. 1, pp. 1567-1576, 1985.
J. Chem. Soc. Perkin, Trans. 1, pp. 1539-1545, 1984.
Tetrahedron, vol. 35, pp. 2181-2185, 1979.
J. Chem. Soc. Perkin Trans. 1, pp. 62-69; 70-76; 84-88.
J. Chem. Soc., Chem. Commun. pp. 635-637; 660-661, 1976.
Tetrahedron Letters, No. 48, pp. 4279-4282, 1975.
J. Chem. Soc., Chem. Commun., 876-877, 1975.
Patent Abstracts of Japan, Band 10, No. 280 (C-374), 24. Sep. 1986; JP-A-61 100 577 (Sagami Chemical Research Centre) 19-05-1986.

Primary Examiner—C. Warren Ivy
Assistant Examiner—Amelia A. Owens
Attorney, Agent, or Firm—Sprung Horn Kramer & Woods

[57] ABSTRACT

Herbicidal 5H-furan-2-one derivatives of the formula

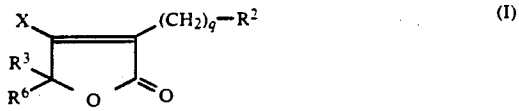

in which
X represents the radical OR$^1$ or the radical

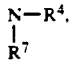

q represents the number 0 or 1,
R$^2$ is optionally substituted aryl, and
R$^3$ and R$^6$ are hydrogen or various organic radicals, with certain provisos and exceptions.

14 Claims, No Drawings

HERBICIDAL 5H-FURAN-2-ONE DERIVATIVES

The invention relates to new 5H-furan-2-one derivatives, to several processes for their preparation, and to their use as herbicides.

It is already known that certain substituted 2H-furan-3-ones, such as, for example, (±)-5-methylamino-2-phenyl-4-[3-trifluoromethyl)-phenyl]-2H-furan-3-one, have herbicidal properties (cf. DE-OS (German Published Specification) 3,422,346).

However, the action of these compounds is not always entirely satisfactory in all fields of application in particular when low amounts or concentrations are used.

The synthesis of numerous 5H-furan-2-one derivatives and their use as intermediates in the synthesis of natural substances are known and thereby excluded from the definition of formula (i) by means of disclaimer (cf. for example, Tetrahedron Lett., 29, 2085–2088, 1988; Can. J. Chem. 64, 104–109, 1986; J. Chem. Soc., Perkin Trans. 1, 1567–76, 1985; J. Chem. Soc. Perkin Trans. 1, 1539–45, 1984; Tetrahedron, 35, 2181–2185, 1979; J. Chem. Soc. Perkin Trans. 1, 70–76, 1979; J. Chem. Soc., Perkin Trans. 1, 62–69, 1979; J. Chem. Soc., Perkin Trans. 1, 84–88, 1979; J. Chem. Soc., Chem. Commun. 660–661, 1976; J. Chem. Soc., Chem. Commun. 635–637, 1976; Tetrahedron Lett. 4279–4282, 1975; J. Chem. Soc., Chem. Commun., 876–877, 1975; JP6917901). However, a herbicidal action of these compounds is not known.

European Patent Application EP-A 299,694 describes furan-2-ones having a fungicidal action.

New 5H-furan-2-one derivatives have now been found, of the formula (I)

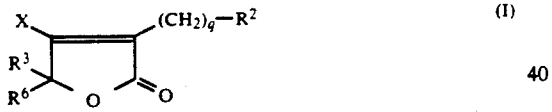

(I)

in which
X represents the radical OR$^1$ or the radical

where
R$^1$ represents alkyl, alkoxyalkyl, cyanoalkyl, alkylcarbonyl, halogenoalkylcarbonyl or alkoxycarbonylalkyl,
R$^4$ represents hydrogen, alkyl, alkenyl, alkoxyalkyl or alkylcarbonyl, and
R$^7$ represents hydrogen, hydroxy, amino, formyl, alkyl, alkoxyalkyl, cyanoalkyl, alkylcarbonyl, halogenoalkylcarbonyl, alkoxycarbonylalkyl, alkoxy, alkylamino, alkylcarbonyloxy, aminocarbonylalkyl, alkynyl, cycloalkyl or arylcarbonyl, aralkyl, aralkyloxy each of which is unsubstituted or substituted, or represents the radical

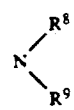

in which R$^8$ and R$^9$ independently of each other are alkyl or alkylcarbonyl or
R$^4$ and R$^7$ together with the nitrogen atom to which they are bonded, represent a saturated heterocycle,
q represents the number 0 or 1,
R$^2$ represents aryl which is unsubstituted or monosubstituted or polysubstituted by identical or different substituents, the substituents selected being: cyano, nitro, halogen, alkyl, alkoxy, halogenoalkyl, halogenoalkoxy, or phenethenyl or phenethynyl each of which is unsubstituted or monosubstituted or polysubstituted by identical or different substituents, phenyl substituents which may be mentioned being cyano, nitro, halogen, alkyl, alkoxy, halogenoalkyl or halogenoalkoxy, and the radical —(CH$_2$)$_n$—Z$_m$—(CH$_2$)$_p$—R$^5$, wherein
R$^5$ represents aryl which is unsubstituted or monosubstituted or polysubstituted by identical or different substituents, substituents which may be mentioned being: cyano, nitro, halogen, alkyl, alkoxy, halogenoalkyl or halogenoalkoxy,
Z represents oxygen, sulphur or the group —CO—,
n, m and p independently of one another represent the numbers 0 or 1, and
R$^3$ and R$^6$ represent hydrogen, alkyl, or aryl or aralkyl each of which are unsubstituted or monosubstituted or polysubstituted by identical or different substituents, substituents in the aryl moiety which are selected being: cyano, nitro, halogen, alkyl, alkoxy, halogenoalkyl or halogenoalkoxy, which the proviso that if X represents the radical OR$^1$ and simultaneously q represents 0, R$^2$ can only represent ortho-substituted phenyl when the substituents are halogen, halogenomethyl having 1 to 3 identical or different halogen atoms or phenyl, phenethenyl or phenethynyl each of which is unsubstituted or monosubstituted to polysubstituted by identical or different substituents, with the proviso that R$^2$ represents substituted phenyl when q represents 1 and X simultaneously represents the radical OR$^1$, and with the exception of the compounds 5-[(3,4-dimethoxyphenyl [methyl]-4-methoxy-3-(4-methoxyphenyl)-5H-furan-2-one, 4-methoxy-3-(3,4,5-trimethoxyphenyl)-5H-furan-2-one, 3-(3-chlorophenyl)-4-methoxy-5H-furan-2-one, 3-(4-chlorophenyl)-4-methoxy-5H-furan-2-one, 3-(3-fluorophenyl)-4-methoxy-5H-furan-2-one, 3-(4-fluorophenyl)-4-methoxy-5H-furan-2-one, 4-methoxy-3-(3-methoxyphenyl)-5H-furan-2-one, 4-(4-bromophenyl)-4-methoxy-5H-furan-2-one, 3-(3,4-dichlorophenyl)-4-methoxy-5H-furan-2-one, 3-[1,1'-biphenyl]-4-yl-4-methoxy-5H-furan-2-one, 4-methoxy-3-(4-methylphenyl-5H-furan-2-one and 4-methoxy-3-(4-methoxyphenyl)-5H-furan-2-one, 3-(2-chlorophenyl)-4-methoxy-5H-furan-2-one, 3-(2fluorophenyl)-4-methoxy-5H-furan-2-one, 4-methoxy-3-(2-methoxyphenyl)-5H-furan-2-one.

Furthermore, it has been found that the new 5H-furan-2-one derivatives of the formula (I) are obtained when
a) in the event that X in formula (I) represents the radical

and

R$^2$, R$^3$, R$^4$, R$^6$ and q have the abovementioned meanings and

R$^{7-0}$ represents hydrogen, alkyl, alkoxyalkyl, cyanoalkyl, alkoxycarbonylalkyl, alkoxy, amino, alkylamino, hydroxy, aralkyl, aminocarbonylalkyl, cycloalkyl, arylalkyloxy, alkynyl or represents the radical NR$^8$R$^9$, where R$^8$ and R$^9$ have the abovementioned meaning or R$^{7-0}$ and R$^4$ together with the nitrogen atom to which they are bonded, represent a saturated heterocycle, a-α) 5H-furan-2-one derivatives of the formula (II)

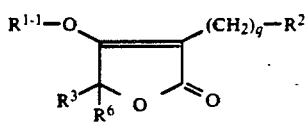  (II)

in which

R$^{1-1}$ represents alkyl, in particular methyl or ethyl, and

R$^2$, R$^3$, R$^6$ and q have the abovementioned meanings, are reacted with amines of the formula (III)

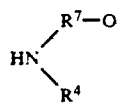  (III)

in which

R$^{7-0}$ and R$^4$ have the abovementioned meanings, or their hydrochlorides, if appropriate in the presence of a diluent and if appropriate under pressure, or a-β) when the 5H-furan-2-one derivatives, obtained by process (a-α), of the formula (Ia)

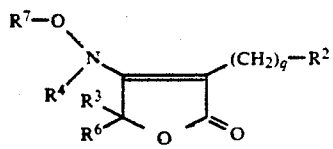  (Ia)

in which R$^{7-0}$, R$^2$, R$^3$, R$^4$, R$^6$ and q have the abovementioned meanings, reacts with acylating agents of the formula (VI)

  (VI)

in which

R$^{7-1}$ represents alkylcarbonyl, alkylcarbonyloxy, halogenoalkylcarbonyl or arylcarbonyl, and E$^2$ represents an electron-attracting leaving group,
or reacts with ortho ester of the formula (VIa)

(RO)$_3$CH  (VIa)

in which R represents methyl or ethyl, if appropriate in the presence of a diluent and if appropriate in the presence of a reaction auxiliary, or when b) in the event that X in formula (I) represents the radical OR$^1$ and R$^1$, R$^2$, R$^3$, R$^6$ and q have the abovementioned meanings, substituted tetronic acid derivatives of the formula (IV)

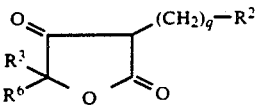

in which R$^2$, R$^3$, R$^6$ and q have the abovementioned meanings, are reacted with alkylating or acylating agents of the formula (V)

R$^1$-E$^1$  (V)

in which

R$^1$ have the abovementioned meaning and

E$^1$ represents an electron-attracting leaving group,
if appropriate in the presence of a diluent and if appropriate in the presence of a catalyst or reaction auxiliary.

Finally, it has been found that the new substituted inert 5H-furan-2-one derivatives of the formula (I) have interesting herbicidal properties.

Surprisingly, the new substituted 5H-furan-2-one derivatives of the formula (I) have better herbicidal properties than (±)-5-methylamino-2-phenyl-4-[-3-(trifluoromethyl)-phenyl[-2H-furan-3-one, which is known from the prior art and is an active compound of a similar constitution and the same type of action.

The invention preferably relates to compounds of the formula (I)

in which

X represents the radical OR$^1$ or the radical

where

R$^4$ represents hydrogen, in each case straight-chain or branched alkyl having 1 to 4 carbon atoms, alkenyl having 2 to 4 carbon atoms or alkoxyalkyl having in each case 1 to 4 carbon atoms in the alkoxy moiety and alkyl moiety or alkylcarbonyl having 1 to 4 carbon atoms, and R$^7$ represents hydrogen, hydroxy, amino, formyl or in each case straight-chain or branched alkyl, alkoxy, alkoxyalkyl, cyanoalkyl, alkylcarbonyl, halogenoalkylcarbonyl, alkoxycarbonyl, alkylamino, alkylcarbonyloxy or aminocarbonylalkyl having 1 to 6 carbon atoms in the individual alkyl moieties and where appropriate 1 to 4 identical or different halogen atoms, or represents alkylnyl having 2 to 8 carbon atoms, or represents cycloalkyl having 3 to 7 carbon atoms, or represents arylcarbonyl, aralkyl, aralkyloxy having 3 to 10 carbon atoms in the aryl part and 1 to 4 carbon atoms in the straight-chain or branched alkyl part, each of which is unsubstituted or monosubstituted or polysubstituted by identical or different substituents, suitable substituents in each case being the substituents already mentioned in the definition of R$^5$, or represents the radical NR$^8$R$^9$ in which R$^8$ and R$^9$ independently of each other represents alkyl or alkylcarbonyl having 1 to 4 carbon atoms, or R$^4$ and R$^7$ together with the nitrogen atom to which they are bonded represent a saturated heterocycle having 4 to 5 carbon atoms, and q represents the numbers 0 or 1, $R^1$ represents straight-chain or branched alkyl having 1 to 4 carbon atoms, or represents in each case straight-chain or branched cyanoalkyl, alkoxyalkyl, alkylcarbonyl, halogenoalkylcarbonyl or alkoxycarbonyl having 1 to 6 carbon atoms in the individual alkyl moieties and where appropriate 1 to 9 identical or different halogen atoms, $R^2$ represents phenyl which is unsubstituted or monosubstituted or polysubstituted by identical or different substituents, substituents which may be mentioned being: cyano, nitro, halogen, in each case straight-chain or branched alkyl or alkoxy having 1 to 6 carbon atoms, in each case straight-chain or branched halogenoalkyl or halogenoalkoxy having 1 to 4 carbon atoms and 1 to 9 identical or different halogen atoms, or phenethenyl or phenethynyl each of which is unsubstituted or monosubstituted or polysubstituted by identical or different substituents, suitable substituents in each case being the phenyl substituents already mentioned above; another phenyl substituent which may be mentioned is the radical $-(CH_2)_n-Z_m-(CH_2)_p-R^5$, where $R^5$ represents aryl which has 6 to 10 carbon atoms, in particular phenyl or naphthyl, and which is unsubstituted or monosubstituted or polysubstituted by identical or different substituents, suitable substituents being cyano, nitro, halogen, $C_{1-4}$-alkyl, $C_{1-4}$-alkoxy, halogeno-$C_{1-4}$-alkyl or halogeno-$C_{1-4}$-alkoxy, Z represents oxygen or sulphur or represents the group $>C=O$ and n, m and p independently of one another represent the numbers 0 or 1, and $R^3$ and $R^6$ represent hydrogen, straight-chain or branched alkyl having 1 to 6 carbon atoms, phenyl which is unsubstituted or monosubstituted to polysubstituted by identical or different substituents, or aralkyl which has 6 to 10 carbon atoms in the aryl moiety and 1 to 4 carbon atoms in the alkyl moiety and which is unsubstituted or monosubstituted to polysubstituted by identical or different substituents, suitable substituents being cyano, nitro, halogen, $C_{1-4}$-alkyl, $C_{1-4}$-alkoxy, halogeno-$C_{1-4}$-alkyl and halogeno-$C_{1-4}$-alkoxy, with the proviso, that if X represents the radical $OR^1$ and simultaneously q represents O, $R^2$ can only represent ortho-substituted phenyl when the substituents are halogen, halogenomethyl having 1 to 3 identical or different halogen atoms or phenyl, phenethenyl or phenethynyl each of which is unsubstituted or monosubstituted to polysubstituted by identical or different substituents, with the proviso that $R^2$ represents substituted phenyl when q represents 1 and X simultaneously represents the radical $OR^1$, and with the exception of the compounds 5-[3,4-dimethoxyphenyl]-methyl]-4-methoxy-3-(4-methoxyphenyl)-5H-furan-2-one, 4-methoxy-3-(3,4,5-trimethoxyphenyl)-5H-furan-2-one, 3-(3-chlorophenyl)-4-methoxy-5H-furan-2-one, 3-(4-chlorophenyl)- f-methoxy-5H-furan-2-one, 3-(3-fluorophenyl)-4-methoxy-5H-furan-2-one, 3-(4-fluorophenyl)-4-methoxy-5H-furan-2-one, 4-methoxy-3-(3-methoxyphenyl)-5H-furan-2-one, 4-(4-bromophenyl)-4-methoxy-5H-furan-2-one, 3-(3,4-dichlorophenyl)-4-methoxy-5H-furan-2-one, 3[1,1'-biphenyl]-4-yl-4-methoxy-5H-furan-2-one, 4-methoxy-3-(4-methylphenyl-5H-furan-2-one and 4-methoxy-3-(4-methoxyphenyl)-5H-furan-2-one, 3-(2-chlorophenyl)-4-methoxy-5H-furan-2-one, 3-(2-fluorophenyl)-4-methoxy-5H-furan-2-one and 4-methoxy-3-(2-methoxyphenyl)-5H-furan-2-one.

Particularly preferred is the group of compounds of the formula (I) in which

X represents the radical

where $R^4$ represents hydrogen, methyl, ethyl, n- or i-propyl, n-, i-, s- or t-butyl, allyl, 2-propenyl, 1-methallyl, methoxymethyl, ethoxymethyl, methyloxyethyl, ethoxyethyl, methylcarbonyl, ethylcarbonyl, n-propylcarbonyl, i-propylcarbonyl, and $R^7$ represents hydrogen, hydroxy, amino, formyl, methyl, ethyl, n- or i-propyl, n-, i-, s- or t-butyl, methoxy, ethoxy, n- or i-propoxy, n-, i-, s- or t-butoxy, alkylcarbonyl having 1 to 6 carbon atoms, or represents in each case straight-chain or branched alkoxyalkyl, cyanoalkyl, halogenoalkylcarbonyl, alkoxycarbonylalkyl, alkylamino, alkylcarbonyloxy or aminocarbonylalkyl having 1 to 4 carbon atoms in the individual alkyl moieties and where appropriate 1 to 9, preferably 1 to 5, identical or different halogen atoms, or represents alkynyl having 2 to 4 carbon atoms, or represents cycloalkyl having 3 to 6 carbon atoms, or represents phenylcarbonyl, phenylalkyl, phenylalkoxy having 1 to 4 carbon atoms in the straight-chain or branched alkyl part, each of which is unsubstituted or monosubstituted to trisubstituted by identical or different substituents, suitable substituents in each case being the substituents already mentioned in the definition of $R^5$, or X represents the radical $NR^8R^9$ in which $R^8$ and $R^9$ in each case independently of each other represent methyl ethyl, n- or i-propyl, methylcarbonyl, ethylcarbonyl or n- or i-propylcarbonyl, or $R^4$ and $R^7$ together with the nitrogen atom to which they are bound represent a saturated nitroalkylene chain having 4 to 5 carbon atoms, q represents the numbers 0 or 1, $R^2$ represents phenyl which is unsubstituted or monosubstituted to trisubstituted by identical or different substituents, suitable substituents which may be mentioned being: cyano, nitro, fluorine, chlorine, bromine, methyl, ethyl, n- or i-propyl, methoxy, ethoxy, n- or i-propoxy, in each case straight-chain or branched halogenoalkyl or halogenoalkoxy having 1 or 2 carbon atoms and 1 to 5 identical or different fluorine or chlorine atoms, or phenethenyl or phenethynyl each of which is unsubstituted or monosubstituted to trisubstituted by identical or different substituents, suitable substituents in each case being the phenyl substituents already mentioned above; as another phenyl substituent, the radical $-(CH_2l)_n- Z_m-(CH_2l)_p-R^5$ may also be mentioned, where $R^5$ represents phenyl which is unsubstituted or monosubstituted to trisubstituted by identical or different substituents, suitable substituents being cyano, nitro, fluorine, chlorine, bromine, methyl, ethyl, n- or i-propyl, methoxy, ethoxy, n- or i-propoxy and in each case straight-chain or branched halogenoalkyl or halogenoalkoxy having 1 or 2 carbon atoms and 1 to 5 identical or different fluorine or chlorine atoms, Z represents oxygen or sulphur or represents the group $>C=O$, and n, m and p independently of one another represent the numbers 0 or 1, $R^3$ and $R^6$ represent hydrogen, methyl, ethyl, n- or i-propyl, n-, i-, s- or t-butyl, phenyl which are unsubstituted or monosubstituted to trisubstituted by identical or different substituents, or benzyl or phenethyl each of which is unsubstituted or monosubstituted to trisubstituted by identical or different substituents, suitable substituents being cyano, nitro, fluorine, chlorine, bromine, methyl, ethyl, n- or i-propyl, methoxy, ethoxy, n- or i-propoxy, and in each case straight-chain or branched halogenoalkyl or halogenoalkoxy having 1 or 2 carbon atoms and 1 to 5 identical or different fluorine or chlorine atoms.

Particularly preferred is also the group of compounds of the formula (I) in which X represents the radical $OR^1$ where $R^1$ represents straight-chain or branched alkyl having 1 to 4 carbon atoms, or represents in each case straight-chain or branched cyanoalkyl, alkoxyalkyl, alkylcarbonyl, halogenoalkylcarbonyl or alkoxycarbonylalkyl having 1 to 6 carbon atoms in the individual alkyl moieties and where appropriate 1 to 9 identical or different halogen atoms, $R^3$ and $R^6$ represent hydrogen, straight-chain or branched alkyl having 1 to 6 carbon atoms, phenyl which are unsubstituted or monosubstituted to polysubstituted by identical or different substituents, or aralkyl which has 6 to 10 carbon atoms in the aryl moiety and 1 to 4 carbon atoms in the alkyl moiety and which is unsubstituted or monosubstituted or polysubstituted by identical or different substituents, suitable substituents being cyano, nitro, halogen, $C_{1-4}$-alkyl, $C_{1-4}$-alkoxy, halogeno-$C_{1-4}$-alkyl and halogeno-$C_{1-4}$-alkoxy, and either

α)

$R^2$ represents phenyl which is mono-, di- or trisubstituted in the meta- or para-position by identical or different substituents, substituents which may be mentioned being: cyano, nitro, halogen, in each case straight-chain or branched alkyl or alkoxy having 1 to 6 carbon atoms, in each case straight-chain or branched halogenoalkyl or halogenoalkoxy having 1 to 4 carbon atoms and 1 to 9 identical or different halogen atoms, or phenethenyl or phenethynyl each of which is unsubstituted or monosubstituted to polysubstituted by identical or different substituents, suitable substituents in each case being cyano, nitro, halogen, in each case straight-chain or branched alkyl or alkoxy having 1 to 6, in particular 1 to 4, carbon atoms, and in each case straight-chain or branched halogenoalkyl or halogenoalkoxy having 1 to 4 carbon atoms and 1 to 9 identical or different halogen atoms;

a further phenyl substituent which may be mentioned is the radical $-(CH_2)_n-Z_m-(CH_2)_p-R^5$, where $R^5$ represents aryl which has 6 to 10 carbon atoms and which is unsubstituted or monosubstituted to polysubstituted by identical or different substituents, suitable substituents being cyano, nitro, halogen, in each case straight-chain or branched alkyl or alkoxy having 1 to 6, in particular 1 to 4, carbon atoms, or in each case straight-chain or branched halogenoalkyl or halogenoalkoxy having 1 to 4 carbon atoms and 1 to 9 identical or different halogen atoms, Z represents oxygen or sulphur, or represents the group $>C=O$, and n, m and p represent the numbers 0 or 1, and q represents the numbers 0 or 1, with the exception of the compounds 5-[(3,4-dimethoxyphenyl-methyl]4-methoxy-3-(4-methoxyphenyl)-5H-furan-2-one, 4-methoxy-3-(3,4,5-trimethoxyphenyl)-5H-furan-2-one, 3-(3-chlorophenyl)-4-methoxy-5H-furan-2-one, 3-(4-chlorophenyl)-4-methoxy-5H-furan-2-one, 3-(3-fluorophenyl)-4-methoxy-5H-furan-2-one, 3-(4-fluorophenyl)-4-methoxy-5H-furan-2-one, 4-methoxy-3-(3-methoxyphenyl)-5H-furan-2-one, 4-(4-bromophenyl)-4-methoxy-5H-furan-2-one, 3-(3,4-dichlorophenyl)-4-methoxy-5H-furan-2-one, 3-[1,1'-biphenyl]-4-yl-4-methoxy-5H-furan-2-one, 4-methoxy-3-(4-methylphenyl)-5H-furan-2-one and 4-methoxy-3-(4-methoxyphenyl)-5H-furan-2-one (cf. Tetrahedron Lett., 29 (17), 1085-8, 1988; J. Che. Soc., Chem. Commun. (16), 660-1, 1976; J. Chem. Soc., Perkin Trans. 1, (8), 1567-76, 1985), or

β)

$R^2$ represents phenyl which is monosubstituted in the ortho-position, substituents which may be mentioned being: cyano, nitro, halogen, in each case straight-chain or branched alkyl or alkoxy having 1 to 6, in particular 1 to 4, carbon atoms, in each case straight-chain or branched halogenoalkyl or halogenoalkoxy having 1 to 4 carbon atoms and 1 to 9 identical or different halogen atoms, or phenethenyl or phenethynyl each of which is unsubstituted or monosubstituted to polysubstituted by identical or different substituents, suitable substituents in each case being cyano, nitro, halogen, in each case straight-chain or branched alkyl or alkoxy having 1 to 6, in particular 1 to 4, carbon atoms, in each case straight-chain or branched halogenoalkyl or halogenoalkoxy having 1 to 4 carbon atoms and 1 to 9 identical or different halogen atoms; another phenyl substituent which may furthermore be mentioned is the radical $-(CH_2l)_n-Z_m-(CH_2)_p-R^5$, $R^5$ represents aryl which has 6 to 10 carbon atoms and which is unsubstituted or monosubstituted to polysubstituted by identical or different substituents, suitable substituents being cyano, nitro, halogen, in each case straight-chain or branched alkyl or alkoxy having 1 to 6, in particular 1 to 4, carbon atoms, and in each case straight-chain or branched halogenoalkyl or halogenoalkoxy having 1 to 4 carbon atoms and 1 to 9 identical or different halogen atoms, Z represents oxygen or sulphur, or represents the group >C=O, and n, m and p represent the numbers 0 or 1 and q represents the number 1 or γ)
R$^2$ represents phenyl which is monosubstituted in the ortho-position, substituents which may be mentioned being: halogen, halogenomethyl having 1 to 3 identical or different halogen atoms, or phenyl, phenethenyl or phenethynyl, each of which is unsubstituted or monosubstituted to polysubstituted by identical or different substituents, suitable substituents in each case being cyano, nitro, halogen, in each case straight-chain or branched alkyl or alkoxy having 1 to 6, in particular 1 to 4, carbon atoms, in each case straight-chain or branched halogenoalkyl or halogenoalkoxy having 1 to 4 carbon atoms and 1 to 9 identical or different halogen atoms, and q represents the number 0, with the exception of the compounds 3-(2-chlorophenyl)-4-methoxy-5-H-furan-2-one, 3-(2-fluorophenyl)-4-methoxy-5H-furan-2-one and 4-methoxy-3-(2-methoxyphenyl)-5H-furan-2-one (cf. J. Chem. Soc., Perkin Trans. 1, (8) 1567–76, 1985).

Very particularly preferred is the group of compounds of the formula (I) in which X represents the radical OR$^1$ where R$^1$ represents methyl, ethyl, n- or i-propyl or n-, i-, s- or t-butyl, or represents in each case straight-chain or branched cyanoalkyl, alkoxyalkyl or alkoxycarbonylalkyl having 1 to 4 carbon atoms in the individual alkyl moieties, R$^3$ and R$^6$ represent hydrogen, methyl, ethyl, n- or i-propyl, n-, i-, s- or t-butyl, phenyl which is unsubstituted or monosubstituted to trisubstituted by identical or different substituents, or benzyl or phenethyl, each of which is unsubstituted or monosubstituted to trisubstituted by identical or different substituents, suitable substituents in each case being cyano, nitro, fluorine, chlorine, bromine, methyl, ethyl, n- or i-propyl, methoxy, ethoxy, n- or i-propoxy, or in each case straight-chain or branched halogenoalkyl or halogenoalkoxy having 1 or 2 carbon atoms and 1 to 5 identical or different fluorine or chlorine atoms; and either α)
R$^2$ represents phenyl which is monosubstituted, di- or trisubstituted in the meta- or para-position by identical or different substituents, substituents which may be mentioned being: cyano, nitro, fluorine, chlorine, bromine, methyl, ethyl, n- or i-propyl, methoxy, ethoxy, n- or i-propoxy, in each case straight-chain or branched halogenoalkyl or halogenoalkoxy having 1 or 2 carbon atoms and 1 to 5 identical or different fluorine or chlorine atoms, or phenylethenyl or phenethynyl, each of which is unsubstituted or monosubstituted to trisubstituted by identical or different substituents, suitable substituents in each case being cyano, nitro, fluorine, chlorine, bromine, methyl, ethyl, n- or i-propyl, methoxy, ethoxy, n- or i-propoxy, or in each case straight-chain or branched halogenoalkyl or halogenoalkoxy having 1 or 2 carbon atoms and 1 to 5 identical or different fluorine or chlorine atoms;

as another phenyl substituent, the radical —(CH$_2$)$_n$—Z$_m$—(CH$_2$)$_p$—R$^5$ may also be mentioned, where R$^5$ represents phenyl which is unsubstituted or monosubstituted to trisubstituted by identical or different substituents, suitable substituents being cyano, nitro, fluorine, chlorine, bromine, methyl, ethyl, n- or i-propyl, methoxy, ethoxy, n- or i-propoxy or in each case straight-chain or branched halogenoalkyl or halogenoalkoxy having 1 or 2 carbon atoms and 1 to 5 identical or different fluorine or chlorine atoms;

Z represents oxygen or sulphur, or represents the group >C=O and n, m and p represent the numbers 0 or 1 and q represents the numbers 0 or 1, with the exception of the compounds 5-[(3,4-dimethoxyphenyl-methyl]-4-methoxy-3-(4-methoxyphenyl)-5H-furan-2-one, 4-methoxy-3-(3,4,5-trimethoxyphenyl)-5H-furan-2-one, 3-(3-chlorophenyl)-4-methoxy-5H-furan-2-one, 3-(4-chlorophenyl)-4-methoxy-5H-furan-2-one, 3-(3-fluorophenyl)-4-methoxy-5H-furan-2-one, 3-(4-fluorophenyl)-4-methoxy-5H-furan-2-one, 4-methoxy-3-(3-methoxyphenyl)-5H-furan-2-one, 4-(4-bromophenyl)-4-methoxy-5H-furan-2-one, 3-(3,4-dichlorophenyl)-4-methoxy-5H-furan-2-one, 3-[1,1'-biphenyl]-4-yl-4-methoxy-5H-furan-2-one, 4-methoxy-3-(4-methylphenyl)-5H-furan-2-one and 4-methoxy-3-(4-methoxyphenyl)-5H-furan-2-one (cf. Tetrahedron Lett., 29 (17), 2085–8, 1988; J. Chem. Soc., Chem. Commun. (161), 660–1, 1976; J. Chem. Soc., Perkin Trans. 1, (8), 1567–76, 1985), or β)
R$^2$ represents phenyl which is monosubstituted in the ortho-position, substituents which may be mentioned being: cyano, nitro, fluorine, chlorine, bromine, methyl, ethyl, n- or i-propyl, methoxy, ethoxy, n- or i-propoxy, in each case straight-chain or branched halogenoalkyl or halogenoalkoxy having 1 or 2 carbon atoms and 1 to 5 identical or different fluorine or chlorine atoms, or phenethenyl or phenethynyl, each of which is unsubstituted or monosubstituted to trisubstituted by identical or different substituents, suitable substituents in each case being cyano, nitro, fluorine, chlorine, bromine, methyl, ethyl, n- or i-propyl, methoxy, ethoxy, n- or i-propoxy, or in each case straight-chain or branched halogenoalkyl or halogenoalkoxy having 1 or 2 carbon atoms and 1 to 5 identical or different fluorine or chlorine atoms, · another phenyl substituent which may furthermore be mentioned is the radical —(CH$_2$)$_n$—Z$_m$—(CH$_2$)$_p$—R$^5$ where R$^5$ represents phenyl which is unsubstituted or monosubstituted to polysubstituted by identical or different substituents, suitable substituents being cyano, nitro, fluorine, chlorine, bromine, methyl, ethyl, n- or i-propyl, methoxy, ethoxy, n- or i-propoxy, or in each case straight-chain or branched halogenoalkyl or halogenoalkoxy having 1 or 2 carbon atoms and 1 to 5 identical or different fluorine or chlorine atoms;

Z represents oxygen or sulphur or represents the group >C=O and n, m and p represent the numbers 0 or 1, and q represents the number 1, or

γ)

R² represents phenyl which is monosubstituted in the ortho-position, the following being mentioned as substituents: fluorine, chlorine, bromine, halogenomethyl having 1 to 3 identical or different fluorine or chlorine atoms, phenyl, phenethenyl or phenethynyl, each of which is unsubstituted or monosubstituted to trisubstituted by identical or different substituents, suitable substituents in each case being cyano, nitro, fluorine, chlorine, bromine, methyl, ethyl, n- or i-propyl, methoxy, ethoxy, n- or i-propoxy, or in each case straight-chain or branched halogenoalkyl or halogenoalkoxy having 1 or 2 carbon atoms and 1 to 5 identical or different fluorine or chlorine atoms, and q represents the number 0, with the exception of the compounds 3-(2-chlorophenyl)-4-methoxy-5H-furan-2-one, 3-(2-fluorophenyl)-4-methoxy-5H-furan-2-one, 4-methoxy-3-(2-methoxyphenyl)-5H-furan-2-one (cf. J. Chem. Soc., Perkin Trans. 1, (8) 1567-76, 1985).

Very particularly preferred is the group of compounds of the formula (I) in which X represents the radical

where

R⁴ represents hydrogen, methyl, ethyl or n- or i-propyl, methylcarbonyl or ethylcarbonyl, and R⁷ represents hydrogen, hydroxy, amino, formyl, methyl, ethyl, n- or i-propyl, n-, i-, s- or t-butyl, methoxy, ethoxy, n- or i-propoxy, n-, i-, s- or t-butoxy, methoxymethyl, ethoxymethyl, methoxyethyl, ethoxyethyl, cyanomethyl, cyanoethyl, methylcarbonyl, ethylcarbonyl, n- or i-propylcarbonyl, n-, i-, s- or t-butylcarbonyl, halogenoalkylcarbonyl having 1 or 2 carbon atoms and 1 to 5 identical or different fluoro- or chloro atoms, methoxycarbonylmethyl, ethoxycarbonylmethyl, methoxycarbonylmethyl, ethoxycarbonylethyl, methylamino, ethylamino, n- or i-propylamino, methylcarbonyloxy, ethylcarbonyloxy, n- or i-propylcarbonyloxy, aminocarbonylmethyl, cyclopropyl, cyclopentyl, cyclohexyl, phenylcarbonyl, phenylalkyl, and phenylalkyloxy in each case having 1 or 2 carbon atoms in the individual alkyl part, or represents the radical NR⁸R⁹, in which R⁸ and R⁹ independently of each other represent in each case methyl, ethyl or methylcarbonyl, or R⁴ and R⁷ together with the nitrogen atom, to which they are bound represent a saturated heteroalkylene chain having 4 to 5 carbon atoms, q represents the number 0 or 1, R² represents phenyl which is unsubstituted or monosubstituted to trisubstituted by identical or different substituents, where at least one of the substituents from the series comprising trifluoromethyl, trifluoromethoxy, fluorine, chlorine and bromine is in the meta-position and, if appropriate, other substituents from the series comprising fluorine, chlorine, bromine, methyl, ethyl or n- or i-propyl are in the ortho- and para-position; another phenyl substituent which may be mentioned is the radical —(CH₂)$_n$—Z$_m$—(CH₂)$_p$—R⁵, where R⁵ represents phenyl which is unsubstituted or monosubstituted to trisubstituted by identical or different substituents, suitable substituents being fluorine, chlorine, bromine, trifluoromethyl, trifluoromethoxy, methyl, ethyl or n- or i-propyl, Z represents oxygen or sulphur or represents the group >C=O, n, m and p represent the numbers 0 or 1, and R³ and R⁶ represent hydrogen, methyl, ethyl, n- or i-propyl, n-, i-, s- or t-butyl, or phenyl or benzyl, each of which is unsubstituted or monosubstituted or disubstituted by identical or different substituents, suitable substituents in each case being fluorine, chlorine, bromine, methyl, ethyl, n- or i-propyl, trifluoromethyl or trifluoromethoxy.

If, for example, 4-methoxy-3-(3-trifluoromethylphenyl)-5H-furan-2-one and dimethylamine hydrochloride are used as starting substances, the course of the reaction for the preparation of the substituted 5H-furan-2-one derivatives of the formula (I) according to process variant a-α) (for example for R¹=R⁴=CH₃, and X=NR⁴) can be described by the following equation:

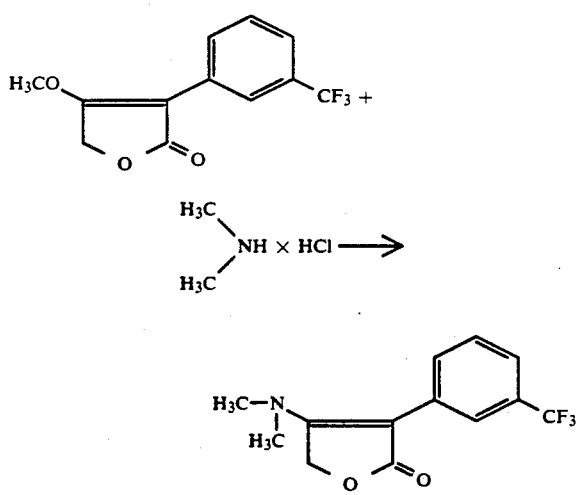

If, for example, 4-amino-3-(3-trifluoromethylphenyl)-5H-furan-2-one and acetyl chloride are used as starting substances, the course of the reaction of process (a-β) according to the invention can be described by the following equation:

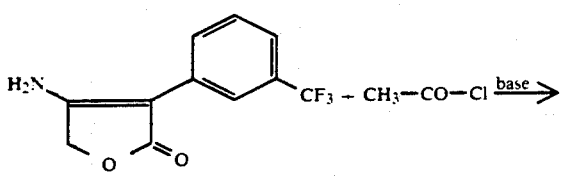

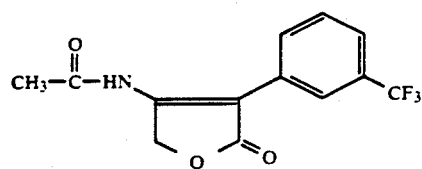

If, for example, 3-(3-trifluoromethylphenyl)-tetronic acid and dimethyl sulphate are used as starting substances and tetrabutylammonium hydroxide as the catalyst, the course of the reaction for the preparation of the substituted 5H-furan-2-one derivatives of the formula (I) according to process variant b) (for example for $R^1=CH_3$ and $X=O$) can be described by the following equation:

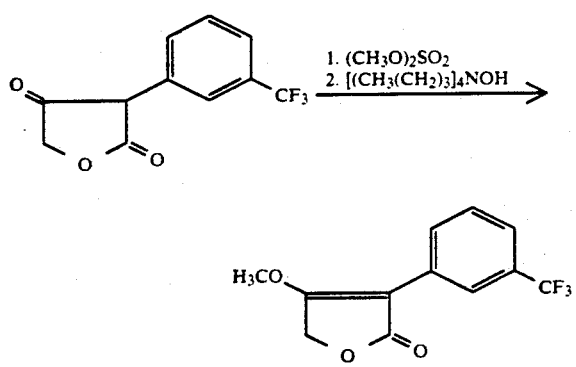

Some of the 5H-furan-2-one derivatives of the formula (II) which are required as starting substances according to process variant a-α), in which formula

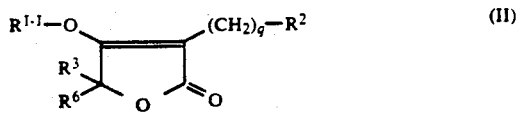

$R^{1-1}$, $R^2$, $R^3$, $R^6$ and q have the meanings which have already been mentioned for these substituents in connection with the description of the substances of the formula (I), are known (cf., for example, Tetrahedron Lett., 29, 2085-2088, 1988; Can. J. Chem., 64, 104-109, 1986; J. Chem. Soc., Perkin Trans. 1, 1567-76, 1985; J. Chem. Soc. Perkin Trans. 1, 1539-45, 1984; Tetrahedron, 35, 2181-2185, 1979; J. Chem. Soc. Perkin Trans. 1, 70-76, 1979; J. Chem. Soc., Perkin Trans. 1, 62-69, 1979; J. Chem. Soc., Perkin Trans. 1, 84-88, 1979; J. Chem. Soc., Chem. Commun. 660-661, 1976; J. Chem. Soc., Chem. Commun. 635-637, 1976; Tetrahedron Lett. 4279-4282, 1975; J. Chem. Soc., Chem. Commun., 876-877, 1975; JP6917901) and/or they can be obtained in analogy to known processes.

Formula (III) provides a general definition of the amines furthermore required as starting substances for the preparation of the substituted 5H-furan-2-one derivatives of the formula (I). In this formula (III), $R^{7-0}$ and $R^4$ preferably represent those radicals which have already been mentioned in connection with the description of the substances of the formula (I) according to the invention as being preferred for $R^1$, with the exception of alkylcarbonyl and halogenoalkylcarbonyl, and for $R^4$.

The amines of the formula (III) are generally known compounds of organic chemistry.

The 5H-furan-2-one derivatives of the formula (Ia) required as starting substances for process (a-β) are compounds according to the invention and can be obtained by process (a-α).

The acylating agents of the formula (VI) furthermore required as starting substances are known compounds of organic chemistry.

In formula (VI), $R^{7-1}$ preferably represents alkylcarbonyl or halogenoalkylcarbonyl, in each case having 1 to 6, in particular 1 to 4, carbon atoms and where appropriate 1 to 9, in particular 1 to 5, identical or different halogen atoms (cf. the corresponding definition of $R^7$). $E^2$ preferably represents halogen, in particular chlorine or bromine, alkoxysulphonyloxy having preferably 1 to 4 carbon atoms, in particular methoxysulphonyloxy or ethoxysulphonyloxy, or represents arylsulphonyloxy, in particular p-toluenesulphonyloxy.

Formula (IV) provides a general definition of the substituted tetronic acid derivatives required as starting substances according to process variant b) for the preparation of the substituted 5H-furan-2-one derivatives of the formula (I). In this formula (IV), $R^2$, $R^6$ and q preferably have the meanings which have already been mentioned in the description of the substances of the formula (I) according to the invention as being preferred for these substituents.

The substituted tetronic acid derivatives of the formula (IV) are known in some cases, and/or they can be prepared by processes known in principle (cf., for example, EP-OS (European Published Specification) 259,707, Arch. Pharm. (Weinheim) 291, 100 (1958) and Preparation Examples).

Formula (V) provides a general definition of the alkylating or acylating agents furthermore required as starting substances for carrying out the process according to the invention according to process variant (b). In this formula (V), $R^1$ preferably represents those radicals which have already been mentioned in connection with the description of the substances of the formula (I) according to the invention as being preferred for this substituent.

$E^1$ represents a leaving group customary in alkylating or acylating agents, preferably an optionally substituted alkyl, alkoxy or arylsulphonyloxy radical, such as, for example, a methoxysulphonyloxy radical, an ethoxysulphonyloxy radical or a p-toluenesulphonyloxy radical, or represents halogen, in particular chlorine, bromine or iodine.

The alkylating and acylating agents of the formula (V) are generally known compounds of organic chemistry.

Process (a-α) according to the invention for the preparation of the new substituted 5H-furan-2-one derivatives of the formula (I) is preferably carried out using diluents.

Diluents for this purpose are virtually all inert organic solvents which are customary for this reaction, in particular alcohols, such as methanol or ethanol; ethers, such as diethyl ether, dioxane, tetrahydrofuran, ethylene glycol dimethyl ether or ethylene glycol diethyl ether, or amides, such as dimethylformamide, dimethylacetamide, N-methylformanilide, N-methylpyrrolidone or hexamethylphosphoric triamide.

When carrying out process (a-α) according to the invention for the preparation of the new substituted 5H-furan-2-one derivatives of the formula (I), the reaction temperatures can be varied within a substantial range. In general, the process is carried out at temperatures between 0° C. and 150° C., preferably at temperatures between 20° C. and 140° C.

For carrying out process (a-α) according to the invention for the preparation of the new substituted 5H-furan-2-one derivatives of the formula (I), 1 to 5 moles, preferably 1 to 3 moles, of amine of the formula (III) are generally employed per mole of 5H-furan-2-one derivative of the formula (II).

Process (a-α) according to the invention for the preparation of the new substituted 5H-furan-2-one derivatives of the formula (I) can be carried out at atmospheric pressure, and also under increased pressure. In general, the process is carried out at a pressure of from 1 to 50 bar, preferably at a pressure of from 1 to 10 bar.

In general, the reactions are carried out in a suitable diluent, and the reaction mixture is stirred for several hours at the specifically required temperature. Working-up is carried out in each case by customary methods. In general, a procedure is followed in which the reaction mixture is filtered, the filtrate is concentrated under reduced pressure, and the product is purified by chromatography.

The process according to the invention for the preparation of the new substituted 5H-furan-2-one derivatives of the formula (I), according to process variants (a-β) and (b) is preferably carried out using diluents.

Suitable diluents are all inert organic solvents which are customary for this reaction. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide. If compounds of the formulae (V) and (V) and (VI) are used in liquid form as reactants in processes (a-β) and (b), it is also possible to employ these in appropriate excess to act simultaneously as the diluents.

Suitable reaction auxiliaries for carrying out process (a-β) according to the invention are all inorganic and organic bases which can customarily be used. The following are preferably used: hydrides, hydroxides, amides, carbonates or hydrogen carbonates of alkali metals, such as, for example, sodium hydride, sodium amide, sodium hydroxide, sodium carbonate or sodium hydrogen carbonate, and also tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

When carrying out process (a-β) according to the invention, the reaction temperatures can be varied within a substantial range. In general, the process is carried out at between −20° C. and +150° C., preferably between 0° C. and +100° C.

For carrying out process (a-β) according to the invention, 1 to 20 moles, preferably 1 to 15 moles, of acylating agent of the formula (VI) and if appropriate 1 to 3 moles, preferably 1 to 2 moles, of reaction auxiliary are generally employed per mole of 5H-furan-2-one derivative of the formula (Ia).

If appropriate, the process according to the invention for the preparation of the new substituted 5H-furan-2-one derivatives of the formula (I), according to process variant (b), can also be carried out in a two-phase system, such as, for example, water/toluene or water/dichloromethane, if appropriate in the presence of a phase transfer catalyst.

The following may be mentioned as examples of such catalysts: tetrabutylammonium iodide, tetrabutylammonium bromide, tributyl-methylphosphonium bromide, trimethyl-$C_{13}/C_{15}$-alkylammonium chloride, dibenzyldimethyl-ammonium methylsulphate, dimethyl-$C_{12}/C_{14}$-alkylbenzyl ammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

When carrying out the process according to the invention for the preparation of the new substituted 5H-furan-2-one derivatives of the formula (I) according to process variant b), the reaction temperatures can be varied within a substantial range. In general, the process is carried out at temperatures of between 0° C. and 80° C., preferably at temperatures between 10° C. and 50° C.

For carrying out process (b) according to the invention for the preparation of the new substituted 5H-furan-2-one derivatives of the formula (I), 1.0 to 3 moles, preferably 1.0 to 1.5 moles, of alkylating agent of the formula (V) and 0.1 to 2 moles, preferably 0.5 to 1.5 moles, of catalyst are generally employed per mole of tetronic acid derivative of the formula (IV).

In general, the reactions are carried out in a suitable diluent, and the reaction mixture is stirred for several hours at the specifically required temperature. Working-up is carried out in each case by customary methods. In general, a procedure is followed in which the reaction mixture is either concentrated under reduced pressure and the product is purified by chromatography.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds utilizable according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulusm, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds which can be used according to the invention are highly suitable for selectively combating monocotyledon and dicotyledon weeds in dicotyledon crops, in particular using the pre-emergence method.

Moreover, some of the active compounds to be used according to the invention also have a fungicidal action. They can be employed with good success, in particular against powdery mildew of cereals and Oomycetes.

Depending on their particular physical and/or chemical properties, the active compounds which can be used according to the invention can be converted into the customary formulations, such as solutions, emulsions, suspensions, powders, foams, pastes, granules, aerosols very fine capsules in polymeric substances and in coating composition for seeds, as well as ULV warm-mist and cold-mist formulations.

These formulations are produced in a known manner, for example by mixing the active compounds with extenders, that is liquid solvents, liquefied gases under pressure, and/or solid carriers, optionally with the use of surface-active agents, that is emulsifying agents and/or dispersing agents and/or foam-forming agents. In the case of the use of water as an extender, organic solvents, for example, can also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propanel, nitrogen and carbon dioxide; as solid carriers there are suitable: for example ground natural minerals, such as kaoline, clays, talc, chalk, quartz, attapulgite, montmorillonite or diatomaceous earth, and ground synthetic minerals, such as highly-disperse silicic acid, alumina and silicates; as solid carriers for granules there are suitable; for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example nonionic and anionic emulsifiers, such a polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulation. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and tracer nutrients such as salts of iron, manganese, boron, copper, cobalt, molybdenum and zinc.

The formulations in general contain between 0.1 and 95 per cent by weight of active compound, preferably between 0.5 to 90%.

For combating weeds, the active compounds according to the invention, as such or in the form of their formulations, can also be used as mixtures with known herbicides, finished formulations or tank mixes being possible.

Suitable components for the mixtures are known herbicides, such as, for example, 1-amino-6-ethylthio-3(2,2-dimethylpropyl)-1,3,5-triazine-2,4(1H,3H)-dione (AMETHYDIONE) or N-(2-benzothiazolyl)-N,N'-dimethyl--urea (META-BENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethyl-ethyl)-3-methylthio-1,2,4-triazin-5(4H)-one (METRIBUZIN) for combating weeds in soy beans. Mixtures with 4-(2,4-dichlorphenoxy)-butyric acid (2,4-DB); N-(methoxymethyl)-2,6-diethylchloroacetanilide (ALACHLOR); 3-isopropyl-2,1,3-benzothiadiazin-4-one 2,2-dioxide (BENTAZONE); ethyl 2-{[(4-chloro-6-methoxy-3-pyrimidinyl)-aminocarbonyl]aminosulphonyl}-benzoate (CHLORIMURON); exo-1-methyl-4-(1-methylethyl)-2-(2-methylphenylmethoxy)-7-oxabicyclo-(2,2,1)-heptane (CINMETHYLIN); 2-[(2-chlorophenyl)methyl]-4,4-dimethylisoxazolidin-3-one DIMETHANZONE); 4-amino-6-t-butyl-3-ethylthio-1,2,4-triazin- 5(4H)-one (ETHIOZIN); 2-{4-[(6-chloro-2-benzoxazolyl)-oxy]-phenoxy}-propanoic acid, its methyl or its ethyl ester (FENOXAPROP); 2-[4-(5-trifluoromethyl-2-pyridyloxy)-phenoxy]-propanoic acid or its butyl ester (FLUAZIFOP); N,N-dimethyl-N'-(3-trifluoromethylphenyl)-urea (FLUOMETURON); 1-methyl-3-phenyl-5-(3-trifluoromethylphenyl)-4-pyridone (FLURI- DONE): 2-{4-[(3-chloro-5-(trifluoromethyl)-2-pyridinyl)-oxy]-phenoxy}-propanoic acid or its ethyl ester HALOXYFOP); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-(1H)-imidazol-2-yl]-5-ethyl-pyridine-3-carboxylic acid (IMAZETHAPYR); N-methyl-2-(1,3-benzothiazol-2-yloxy)-acetanilide (MEFENACET); 2-chloro-N-(2,6-dimethylphenyl)-N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); N-(1-ethylpropyl)-3,4-dimethyl-2,6-dinitroaniline (PENDIMETHALIN); and ethyl 2-[4-(6-chloroquinoxalin-2-yloxy)-phenoxy]-propionate (QUIZALOFOPETHYL) are also possible.

Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

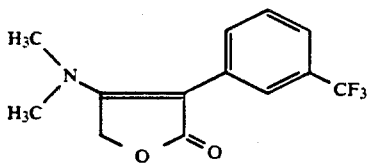

Process variant a-α

5.16 g (0.2 mol) of 4-methoxy-3-(3-trifluoromethylphenyl)-1H-furan-2-one are dissolved in 100 ml of methanol, 0.9 g of dimethylamine, dissolved in 34 ml of xylene, are added, and 0.1 g of dimethylammonium hydrochloride are added. The mixture is heated for 3 hours in the autoclave at 110° C., during which process a pressure of 5 bar is established. After cooling, the pressure is let down, the solution is filtered, and the methanol is distilled off. Chromatography over a silica gel column (eluent: methylene chloride/methanol 10:0.25l) gives an oil which, after having been dissolved in 60 ml of diisopropyl ether, crystallizes in colorless crystals.

This gives 4.3 g (79.3% of theory) of 4-dimethylamino-3-(3-trifluoromethylphenyl)-5H-furan-2-one of melting point 110° C.

Example 2

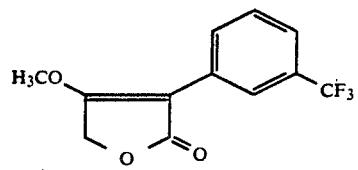

Process variant b 2.44 g (0.01 mol) of 3-(3-trifluoromethylphenyl)-tetronic acid are dissolved in 6.5 g (0.01 mol) of 40% strength aqueous tetrabutylammonium hydroxide solution, 3 ml of water and 4 ml of methylene chloride. The solution is stirred for 2 hours at 20° C., the methylene chloride phase is separated off, the aqueous phase is extracted twice with 5 ml portions of methylene chloride, and the organic phases are combined and dried over sodium sulphate. After the drying agent has been filtered off, 1.05 ml (0.011 mol) of dimethyl sulphate are added dropwise, the mixture is subsequently stirred for 16 hours at 20° C., the solvent is distilled off, and the oil which forms is chromatographed on silica gel with methylene chloride. The oil which forms crystallizes in colourless crystals when 10 ml of diisopropyl ether are added.

This gives 1.5 g (58.1% of theory) of 4-methoxy-3-(3-trifluoromethylphenyl)-5H-furan-2-one of melting point of 126° C.

Example 39

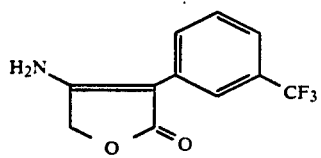

Process variant a-α

2.6 g (0.01 mol) of 4-methoxy-3-(3-trifluoromethylphenyl)-5H-furan-2-one are suspended in 30 ml of methanol. 7 ml (about 0.01 mol) of concentrated ammonia solution are subsequently added. The mixture is stirred for about 18 hours at room temperature, and the clear solution is then evaporated. Chromatography over a silica gel column (eluent: methylene chloride/methanol 10:0.1) gives an oil which crystallizes out. The crystals are stirred with 15 ml of diisopropyl ether and filtered off with suction.

This gives 1.8 g (74% of theory) of 4-amino-3-(3-trifluoromethylphenyl)-5H-furan-2-one of melting point 165° C.

Example 41

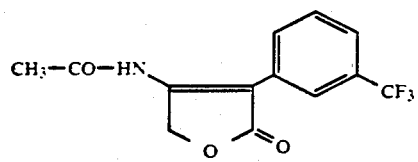

Process variant a β

1.2 g (0.005 mol) of 4-amino-3-(3-trifluoromethyl-phenyl)-5H-furan-2-one (Example 39) are dissolved in 20 ml of acetic anhydrice. 0.1 ml of acetyl chloride are subsequently added, and the mixture is stirred for 22 hours at 130° C. The reaction mixture is then stirred into 100 ml of water, and the mixture is poured off twice using 20 ml portions of methylene chloride. The organic phases are combined and dried with sodium sulphate. After the drying agent has been filtered off, the mixture is evaporated, and the oil which forms is chromatographed on silica gel with methylene chloride. The oil which forms crystallizes in colorless crystals when 10 ml of diisopropyl ether are added.

This gives 0.7 g (49.1% of theory) of 4-methylcarbonylamino-3-(3-trifluoromethylphenyl)-5H-furan-2-one of melting point 140° C.

The end products of the formula (I)

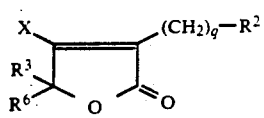

which are listed in Table 1 below are obtained by methods analogous to those described in Examples 1, 2, 39 and 41 and taking into account the instructions in the descriptions of the processes according to the invention.

TABLE 1

| Ex. No. | X | q | $R^2$ | $R^6$ | $R^3$ | Physical constant |
|---|---|---|---|---|---|---|
| 3 | $CH_3-O$ | 0 | 3-(benzyloxy)phenyl | H | H | $n_D^{20} = 1.5852$ |
| 4 | $CH_3-O$ | 1 | 2-(trifluoromethyl)phenyl | H | H | m.p.: 83–85° C. |
| 5 | $CH_3-O$ | 0 | 3-chloro-4-methoxyphenyl | H | H | m.p.: 159–161° C. |
| 6 | $CH_3-O$ | 0 | 3-(trifluoromethyl)phenyl | H | $CH_3$ | m.p.: 81° C. |
| 7 | $CH_3-O$ | 1 | 3-methylphenyl | H | H | $n_D^{20} = 1.5318$ |
| 8 | $CH_3-O$ | 1 | 3,4-dimethoxyphenyl | H | H | m.p.: 94–95° C. |

TABLE 1-continued

| Ex. No. | X | q | R² | R⁶ | R³ | Physical constant |
|---|---|---|---|---|---|---|
| 9 | C₄H₉—O | 0 | 3-CF₃-C₆H₄— | H | H | m.p.: 70° C. |
| 10 | C₂H₅—O | 0 | 3-CF₃-C₆H₄— | H | H | m.p.: 122° C. |
| 11 | CH₃—NH | 0 | 3-CF₃-C₆H₄— | H | H | m.p.: 186° C. |
| 12 | C₄H₉—H | 0 | 3-CF₃-C₆H₄— | H | H | m.p.: 110° C. |
| 13 | C₂H₅—N(CH₃)— | 0 | 3-CF₃-C₆H₄— | H | H | m.p.: 92° C. |
| 14 | CH₃—O | 1 | 2-Cl-C₆H₄— | H | H | m.p.: 71–72° C. |
| 15 | CH₃—O | 1 | 2-CH₃-C₆H₄— | H | H | m.p.: 86–87° C. |
| 16 | CH₃—O | 0 | 2-Cl-C₆H₄— | H | H | m.p.: 96° C. |
| 17 | CH₃—O | 1 | 3-Cl-C₆H₄— | H | H | m.p.: 82–83° C. |
| 18 | CH₃—O | 1 | 4-Cl-C₆H₄— | H | H | m.p.: 60–61° C. |

TABLE 1-continued

| Ex. No. | X | q | R² | R⁶ | R³ | Physical constant |
|---|---|---|---|---|---|---|
| 19 | CH₃—O | 1 | 2,6-dichlorophenyl | H | H | m.p.: 138–139° C. |
| 20 | CH₃—O | 1 | 3-CF₃-phenyl | H | H | $n_D^{20}$ = 1.5003 |
| 21 | C₂H₅—NH | 1 | 3-CF₃-phenyl | H | H | m.p.: 137° C. |
| 22 | CH₃—NH | 1 | 3-CF₃-phenyl | H | H | m.p.: 106° C. |
| 23 | CH₃—NH | 0 | 3-CF₃-phenyl | H | CH₃ | m.p.: 127° C. |
| 24 | CH₃—O | 0 | 3-CF₃-phenyl | H | phenyl | m.p.: 119° C. |
| 25 | CH₃—NH | 0 | 3-CF₃-phenyl | H | phenyl | m.p.: 91° C. |
| 26 | C₂H₅—NH | 0 | 3-CF₃-phenyl | H | H | m.p.: 110° C. |
| 27 | C₃H₇—NH | 0 | 3-CF₃-phenyl | H | H | m.p.: 114° C. |
| 28 | HN—CH₂CH₂—OCH₃ | 0 | 3-CF₃-phenyl | H | H | m.p.: 115° C. |

TABLE 1-continued
| Ex. No. | X | q | R² | R⁶ | R³ | Physical constant |
|---|---|---|---|---|---|---|
| 29 | NH–CH₂–C(=O)OC₂H₅ | 0 | 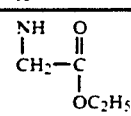 3-CF₃-C₆H₄ | H | H | m.p.: 134° C. |
| 30 | C₂H₅—NC₂H₅ | 0 | 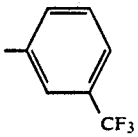 3-CF₃-C₆H₄ | H | H | $n_D^{20}$ = 1.5505 |
| 31 | C₂H₅—NH | 1 | 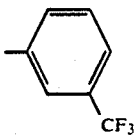 3-Br-C₆H₄ | H | H | m.p.: 131° C. |
| 32 | CH₃—O | 0 | 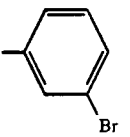 3-CF₃-C₆H₄ | H | C₂H₅ | m.p.: 46° C. |
| 33 | CH₃—O | 0 | 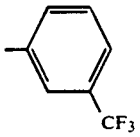 3-CF₃-C₆H₄ | H | C₃H₇ | m.p.: 30° C. |
| 34 | CH₃—O | 0 | 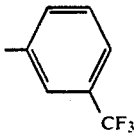 3-CF₃-C₆H₄ | H | C₄H₉ | $n_D^{20}$ = 1.5018 |
| 35 | CH₃—NH | 0 | 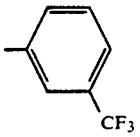 3-CF₃-C₆H₄ | H | C₂H₅ | m.p.: 133° C. |
| 36 | CH₃—NH | 0 | 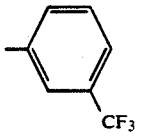 3-CF₃-C₆H₄ | H | C₃H₇ | m.p.: 124° C. |
| 37 | CH₃—NH | 0 | 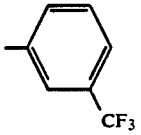 3-CF₃-C₆H₄ | H | C₄H₉ | m.p.: 126° C. |
| 38 | CH₃—O | 0 | 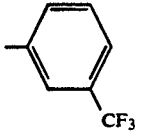 3-CF₃-C₆H₄ | H | —CH₂—C₆H₅ 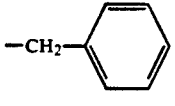 | |

TABLE 1-continued

| Ex. No. | X | q | R² | R⁶ | R³ | Physical constant |
|---|---|---|---|---|---|---|
| 39 | NH₂ | 0 | 3-CF₃-phenyl | H | H | m.p.: 165° C. |
| 40 | CH₃—CO—NCH₃ | 0 | 3-CF₃-phenyl | H | H | m.p.: 120° C. |
| 41 | CH₃—CO—NH | 0 | 3-CF₃-phenyl | H | H | m.p.: 140° C. |
| 42 | CH₃—CO—O | 0 | 3-CF₃-phenyl | H | H | m.p.: 107° C. |
| 43 | NH₂ | 1 | 3-CF₃-phenyl | H | H | |
| 44 | CH₃—C(=O)—N(CH₃)— | 1 | 3-CF₃-phenyl | H | H | |
| 45 | ClCH₂—C(=O)—NH | 0 | 3-CF₃-phenyl | H | CH₃ | $n_D^{23} = 1.5373$ |
| 46 | CH₃—C(=O)—O | 0 | 3-CF₃-phenyl | H | CH₃ | $n_D^{23} = 1.5033$ |
| 47 | CH₃—C(=O)—NH | 0 | 3-CF₃-phenyl | H | C₂H₅ | $n_D^{23} = 1.4937$ |
| 48 | NH₂ | 0 | 3-CF₃-phenyl | H | C₂H₅ | m.p.: 120° C. |

TABLE 1-continued

| Ex. No. | X | q | R² | R⁶ | R³ | Physical constant |
|---|---|---|---|---|---|---|
| 49 | CH₃—C(=O)—NH | 0 | 3-CF₃-C₆H₄- | H | —CH₂—C₆H₅ | $n_D^{23}$ = 1.5519 |
| 50 | CH₃—C(=O)—NH | 0 | 3-CF₃-C₆H₄- | H | C₃H₇ᵢ | $n_D^{23}$ = 1.5417 |
| 51 | C₄H₉ᵢ—C(=O)—NH | 0 | 3-CF₃-C₆H₄- | H | H | m.p.: 208° C. |
| 52 | C₄H₉ᵢ—C(=O)—NH | 0 | 3-CF₃-C₆H₄- | H | CH₃ | m.p.: 121° C. |
| 53 | C₄H₉ᵢ—C(=O)—NH | 0 | 3-CF₃-C₆H₄- | H | H | m.p.: 150° C. |
| 54 | C₃H₇ᵢ—C(=O)—NH | 0 | 3-CF₃-C₆H₄- | H | H | m.p.: 186° C. |
| 55 | ClCH₂—C(=O)—NH | 0 | 2-CF₃-C₆H₄- | H | H | m.p.: 84° C. |
| 56 | C₃H₇ₙ—C(=O)—NH | 0 | 3-CF₃-C₆H₄- | H | H | m.p.: 99° C. |
| 57 | C₂H₅—C(=O)—NH | 0 | 3-CF₃-C₆H₄- | H | H | m.p.: 130° C. |
| 58 | CF₃—C(=O)—NH | 0 | 3-CF₃-C₆H₄- | H | H | m.p.: 128° C. |
| 59 | Cl₃C—C(=O)—NH | 0 | 3-CF₃-C₆H₄- | H | H | $n_D^{23}$ = 1.5187 |

TABLE 1-continued

| Ex. No. | X | q | R² | R⁶ | R³ | Physical constant |
|---|---|---|---|---|---|---|
| 60 | CH₃—C(=O)—NH | 0 | 3-CF₃-C₆H₄ | H | CH₃ | $n_D^{23} = 1.4911$ |
| 61 | NH₂ | 0 | 3-CF₃-C₆H₄ | H | C₃H₇i | m.p.: 139° C. |
| 62 | CH₃O | 0 | 2-CF₃-C₆H₄ | H | 4-F-C₆H₄ | $n_D^{23} = 1.5661$ |
| 63 | CH₃O | 0 | 3-CF₃-C₆H₄ | H | C₃H₇i | $n_D^{23} = 1.5030$ |
| 64 | NH₂ | 0 | 3-CF₃-C₆H₄ | H | CH₂-C₆H₅ | m.p.: 142° |
| 65 | C₂H₅—C(=O)—NH | 0 | 3-CF₃-C₆H₄ | H | CH₃ | m.p.: 54° C. |
| 66 | NH₂ | 0 | 3-CF₃-C₆H₄ | H | CH₃ | m.p.: 124° C. |
| 67 | CH₃—C(=O)—O—N—C(=O)—CH₃ | 0 | 3-CF₃-C₆H₄ | H | CH₃ | $n_D^{23} = 1.5069$ |
| 68 | cyclopropyl-N(—C(=O)CH₃) | 0 | 3-CF₃-C₆H₄ | H | CH₃ | $n_D^{23} = 1.5244$ |
| 69 | cyclopropyl-N(—C(=O)CH₃) | 0 | 3-CF₃-C₆H₄ | H | H | $n_D^{23} = 1.5250$ |
| 70 | CH≡C—CH₂—NH | 0 | 3-CF₃-C₆H₄ | H | H | m.p.: 112° C. |

TABLE 1-continued

| Ex. No. | X | q | R² | R⁶ | R³ | Physical constant |
|---|---|---|---|---|---|---|
| 71 | C₆H₅-CH₂-O-NH | 0 | 3-CF₃-C₆H₄ | H | H | m.p.: 153° C. |
| 72 | C₂H₅-O-NH | 0 | 3-CF₃-C₆H₄ | H | H | m.p.: 129° C. |
| 73 | CH₃O-NH | 0 | 3-CF₃-C₆H₄ | H | H | m.p.: 118° C. |
| 74 | C₆H₅-CH₂-N(COCH₃) | 0 | 3-CF₃-C₆H₄ | H | H | m.p.: 91° C. |
| 75 | C₆H₅-CH₂-CH₂-N(COCH₃) | 0 | 3-CF₃-C₆H₄ | H | H | m.p.: 93° C. |
| 76 | CH₃-C(=O)-O-N(COCH₃) | 0 | 3-CF₃-C₆H₄ | H | H | m.p.: 84° C. |
| 77 | cyclopropyl-NH | 0 | 3-CF₃-C₆H₄ | H | CH₃ | m.p.: 121° C. |
| 78 | HO-NH | 0 | 3-CF₃-C₆H₄ | H | H | m.p.: 161° C. |
| 79 | CH₃NH-NH | 0 | 3-CF₃-C₆H₄ | H | CH₃ | m.p.: 134° C. |
| 80 | NH₂-N(CH₃) / CH₃NH-NH | 0 | 3-CF₃-C₆H₄ | H | CH₃ | m.p.: 171° C. isomer mixture 1:1 |
| 81 | C₆H₅-CH(CH₃)-NH | 0 | 3-CF₃-C₆H₄ | H | H | $n_D^{23} = 1.5771$ |

TABLE 1-continued

| Ex. No. | X | q | R² | R⁶ | R³ | Physical constant |
|---|---|---|---|---|---|---|
| 82 | C₆H₅-CH₂-NH- | 0 | 3-CF₃-C₆H₄- | H | H | m.p.: 61° C. |
| 83 | C₆H₅-CH₂-CH₂NH- | 0 | 3-CF₃-C₆H₄- | H | H | m.p.: 117° C. |
| 84 | C₆H₅-CH₂-NCH₃- | 0 | 3-CF₃-C₆H₄- | H | H | $n_D^{23}$ = 1.5779 |
| 85 | (CH₃CO)₂N-NCH₃ | 0 | 3-CF₃-C₆H₄- | H | H | m.p.: 158° C. |
| 86 | CH₃NH—NCH₃ | 0 | 3-CF₃-C₆H₄- | H | H | m.p.: 132° C. |
| 87 | H₂N—NH | 0 | 3-CF₃-C₆H₄- | H | H | m.p.: 171° C. |
| 88 | H₂N—NCH₃ / CH₃NH—NH | 0 | 3-CF₃-C₆H₄- | H | H | m.p.: 108° C. Isomer mixture 9:1 |
| 89 | C₆H₅-C(O)-NH- | 0 | 2-CF₃-C₆H₄- | H | H | m.p.: 100° C. |
| 90 | HC(O)—NH | 0 | 3-CF₃-C₆H₄- | H | H | m.p.: 133-135° C. |
| 91 | pyrrolidin-1-yl | 0 | 3-CF₃-C₆H₄- | H | H | m.p.: 111° C. |

TABLE 1-continued

| Ex. No. | X | q | R² | R⁶ | R³ | Physical constant |
|---|---|---|---|---|---|---|
| 92 | ▷—NH | 0 | 3-CF₃-C₆H₄ | H | H | m.p.: 118° C. |
| 93 | $\left(CH_3-\underset{O}{\underset{\|}{C}}-\right)_2 N-NCH_3$ <br><br> $CH_3-\underset{O}{\underset{\|}{C}}-\underset{CH_3}{\underset{\|}{N}}-N-\underset{O}{\underset{\|}{C}}-CH_3$ | 0 <br><br><br> 0 | 3-CF₃-C₆H₄ <br><br><br> 3-CF₃-C₆H₄ | CH₃ <br><br><br> CH₃ | H <br><br><br> H | $n_D^{25} = 1.5144$ <br><br><br> Isomer mixture |
| 94 | $NH_2-\underset{O}{\underset{\|}{C}}-CH_2-NH$ | 0 | 3-CF₃-C₆H₄ | H | H | m.p.: 170° C. |
| 95 | CH₃O | 0 | 3-CF₃-C₆H₄ | CH | CH₃ | m.p.: 109° C. |
| 96 | CH₃NH | 0 | 3-CF₃-C₆H₄ | CH₃ | CH₃ | m.p.: 200° C. |
| 97 | CH₃O | 0 | 3-CF₃-C₆H₄ | CH₃ | C₆H₅ | $n_D^{20} = 1.5507$ |

PREPARATION OF THE STARTING COMPOUNDS

Example (IV-1)

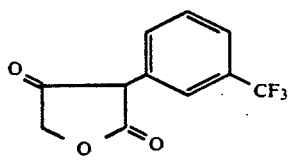

1.9 g (0.017 mol) of potassium tert-butylate are dissolved in 20 ml of butanol, 5.0 g (0.017 mol) of ethyl O-(3-trifluorophenylacetyl)hydroxyacetate are added dropwise, and the mixture is stirred for 16 hours at 80° C. After cooling, the mixture is acidified with 5 ml of concentrated hydrochloric acid and extracted 3 times with 50 ml portions of methylene chloride, and the methylene chloride phase is dried over sodium sulphate. After the solvent has been distilled off under a water pump vacuum, the oil which remains is taken up in 10 ml of diisopropyl ether. During this process, 1.9 g (58.5% of theory) of colorless crystals of 3-(3-trifluoromethylphenyl)-tetronic acid crystallize, melting point 184° C.

Example (IV-2)

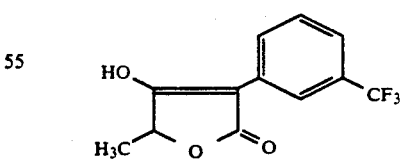

A solution of 13.3 g (42.2 mmol) of ethyl DL-O-(3--trifluoromethylphenylacetyl)-lactate in 20 ml of anhydrous dimethylformamide is added dropwise in the course of 10 minutes to a suspension, cooled in an ice bath at 0°-5° C., of 1.3 g (43.3 mmol) of 80% sodium hydride in paraffin oil in 20 ml of anhydrous dimethylformamide. The mixture is subsequently allowed to warm to room temperature and stirred for 16 hours at this temperature. After this, 10 ml of water are added to the reaction solution, and the mixture is acidified to pH 1 with concentrated hydrochloric acid and extracted by shaking three times with 50 ml portions of dichloromethane. The combined organic phases are extracted by shaking with saturated sodium chloride solution and dried over sodium sulphate, and the solvent is evaporated off in vacuo. The dimethylformamide which remains is distilled off in an oil pump vacuum. The residue obtained is triturated with petroleum ether.

This gives 6.8 g (63% of theory) of DL-4-hydroxy-5-methyl-3-(3-trifluoromethylphenyl)-5H-furan-2-one as a pale yellow solid of melting point 175° C.

Example (IV-3)

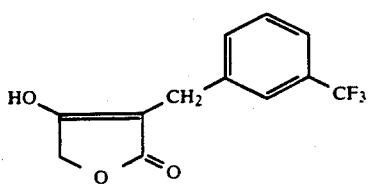

32.0 g (0.125 mol) of 3-(3-trifluoromethylben-zylidene)-2,4-furan-dione are hydrogenated in 450 ml of ethyl acetate in the presence of 4.0 g of palladium/activated carbon (4%) under a hydrogen atmosphere of 9 bar at room temperature. After 90 minutes, the solution is filtered, and the solvent is distilled off. The resulting crude product is recrystallized from diethyl ether.

This gives 16.0 g (50% of theory) of 3-trifluoromethylbenzyl-tetronic acid of melting point 128°-129° C.

The starting compounds of the formula (IV) set forth in the following Table 2 were prepared analogously to the procedures of Examples (IV-1) to (IV-3) and with reference to the examples in the foregoing description relating to process variant (b).

TABLE 2

(IV)

| Ex. No. | q | R² | R³ | R⁶ | Physical constant |
|---|---|---|---|---|---|
| (IV-4) | 0 | 3-CF₃-C₆H₄ | C₆H₅ | H | m.p.: 210° C. |
| (IV-5) | 1 | 3-Br-C₆H₄ | H | H | m.p.: 146-148° C. |
| (IV-6) | 0 | 2-CH₃-C₆H₄ | 4-F-C₆H₄ | H | m.p.: 114° C. |
| (IV-7) | 0 | 3-CF₃-C₆H₄ | C₃H₇i | H | m.p.: 161° C. |
| (IV-8) | 0 | 3-CF₃-C₆H₄ | C₂H₅ | H | n_D²⁰ = 1.4839 |
| (IV-9) | 0 | 3-CF₃-C₆H₄ | C₃H₇n | H | n_D²⁵ = 1.5176 |
| (IV-10) | 0 | 3-CF₃-C₆H₄ | C₄H₉n | H | m.p.: 94° C. |
| (IV-11) | 0 | 3-CF₃-C₆H₄ | CH₂-C₆H₅ | H | n_D²⁵ = 1.5067 |
| (IV-12) | 0 | 3-CF₃-C₆H₄ | C₆H₅ | CH₃ | m.p.: 177° C. |
| (IV-13) | 0 | 2,3-Cl₂-C₆H₃ | CH₃ | H | m.p.: >200° C. |

PREPARATION OF THE PRECURSORS

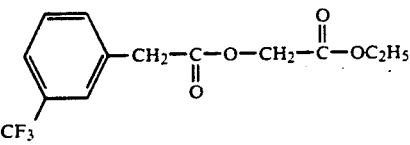

2.4 g (0.105 mol) of sodium are added in portions to 100 ml of ethanol, at 20° C. to 50° C. 21 g (0.105 mol) of 3-trifluorophenylacetic acid are added in portions, the mixture is subsequently stirred for 30 minutes at 20° C., and 11.7 ml (0.105 mol) of ethyl bromoacetate are added dropwise. During this process the temperature rises to 28° C. After this, the mixture is heated to 80° C., and the mixture is subsequently stirred for 2 hours. The solvent is distilled off under a water pump vacuum, the residue is taken up in 300 ml of methylene chloride, the organic phase is washed twice with 150 ml portions of water and dried over sodium sulphate, and the solvent is distilled off under a water pump vacuum after the mixture has been filtered. Chromatography over silica gel (eluent: methylene chloride) gives 28.3 g (93% of theory) of ethyl O-(3-trifluoromethylphenylacetyl)-hydroxyacetate as an oil of refractive index $n_D^{23}=1.4535$.

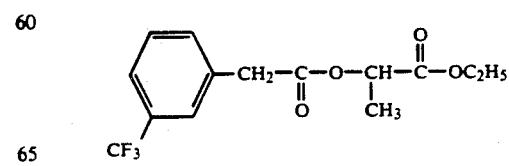

10.0 g (44.9 mmol) of 3-trifluoromethylphenylacetyl chloride and 5.3 g (44.9 mmol) of ethyl DL-lactate are heated slowly to 100° C., and the mixture is stirred at this temperature until the evolution of HCl has ceased. The reaction is complete after 2 hours. The mixture is allowed to cool, and the reaction solution is filtered over a silica gel column (eluent: methylene chloride).

This gives 13.3 g (97% of theory) of ethyl DL-O-(3-trifluoromethylphenylacetyl)-lactate as a pale yellow liquid of refractive index $n_D^{20} = 1.4524$.

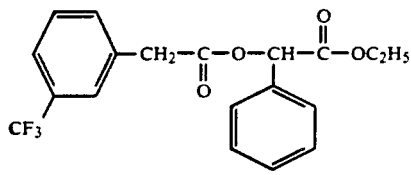

An analogous procedure gives ethyl DL-O-(3-trifluoromethylphenylacetyl)-mandelate as a yellow oil of refractive index $n_D^{20} = 1.4978$.

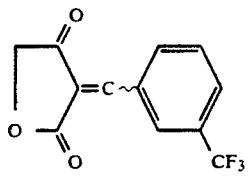

19.4 ml of concentrated hydrochloric acid are added dropwise in the course of 30 minutes to a stirred solution of 104.5 g (0.6 mol) of 3-trifluoromethylbenzaldehyde and 20.0 g (0.2 mol) of tetronic acid in 60 ml of methylene chloride. After 24 hours, the crude product is stirred into 150 ml of saturated sodium hydrogen carbonate solution, the organic phase is separated off, and the aqueous phase is extracted twice with 70 ml portions of methylene chloride. The combined organic phases are dried over sodium sulphate, the solvent is distilled off, and the residue which remains is recrystallized from diisopropyl ether. This gives 38.5 g (75% of theory) of 3-(3-trifluoromethylbenzylidene)-2,4-furandione of melting point 108°–109° C.

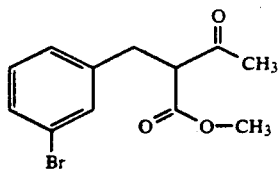

58 g (0.5 mol) of ethyl acetate are rapidly added dropwise to a solution of 13.5 g (0.25 mol) of sodium methylate in 100 ml of methanol, at 30°–35° C. After the mixture is stirred for a short while (20 minutes), 50 g (0.25 mol) of 3-bromobenzyl bromide are added dropwise at 30° C. After the exothermic reaction has ceased, the mixture is heated at the boil for another 4 hours, and the solvent is subsequently distilled off. The residue is treated with 200 ml of water, and the mixture is extracted 3 times with 75 ml of ether. The combined organic phases are dried over sodium sulphate and freed from the solvent. Fractionation of the residue gives 56.0 g (0.20 mol, 80% of theory) of methyl 2-(3-bromobenzyl)acetoacetate of boiling point 105° C./0.1 torr).

USE EXAMPLES

In the Use Example which follows, the compound listed below was used as comparison substance:

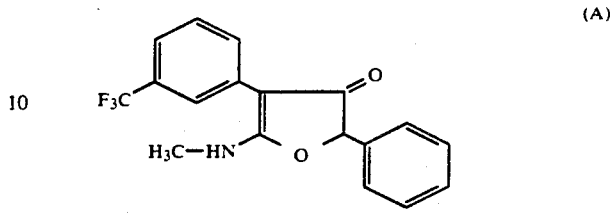

(±)-5-Methylamino-2-phenyl-4-[3-(trifluoromethyl)-phenyl]-2H-furan-3-one (disclosed in De-OS (German Published Specification) 3,422,346, Example 7, page 53).

Example A

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example compound (15) shows a markedly better tolerance by soy beans and cotton and shows a better herbicidal action than comparison compound (A).

Moreover, for example, compound (41) is better tolerated by wheat and shows a markedly better herbicidal action than the comparison compound (A).

It is understood that the specification and examples are illustrative but not limitative of the present invention and that other embodiments with the spirit and scope of the invention will suggest themselves to those skilled in the art.

We claim:
1. A 5H-furan-2-one of the formula

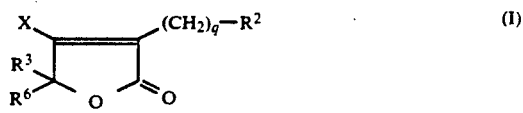

in which
X represents the radical OR[1] or the radical

where
R[1] represents straight-chain or branched alkyl having 1 to 4 carbon atoms, or represents in each case straight-chain or branched cyanoalkyl, alkoxyalkyl, alkylcarbonyl, halogenoalkylcarbonyl or alkoxycarbonyl having 1 to 6 carbon atoms in the individual alkyl moieties and where appropriate 1 to 9 identical or different halogen atoms, R[4] represents hydrogen, in each case straight-chain or branched alkyl having 1 to 4 carbon atoms, alkenyl having 2 to 4 carbon atoms or alkoxyalkyl having in each case 1 to 4 carbon atoms in the alkoxy moiety and alkyl moiety or alkylcarbonyl having 1 to 4 carbon atoms, and R[7] represents hydrogen, hydroxy, amino, formyl or in each case straight-chain or branched alkyl, alkoxy, alkoxyalkyl, cyanoalkyl, alkylcarbonyl, halogenoalkylcarbonyl, alkoxycarbonyl, alkylamino, alkylcarbonyloxy or aminocarbonylalkyl having 1 to 6 carbon atoms in the individual alkyl moieties and where appropriate 1 to 4 identical or different halogen atoms, or represents alkynyl having 2 to 8 carbon atoms, or represents cycloalkyl having 3 to 7 carbon atoms, or represents arylcarbonyl, aralkyl, aralkyloxy having 3 to 10 carbon atoms in the aryl part and 1 to 4 carbon atoms in the straight-chain or branched alkyl part, each of which is unsubstituted or monosubstituted or polysubstituted by identical or different substituents as mentioned in the definition of R[5] hereinbelow, or represents the radical NR[8]R[9] in which R[8] and R[9] independently of each other represents alkyl or alkylcarbonyl having 1 to 4 carbon atoms, or R[4] and R[7] together with the nitrogen atom to which they are bonded represent a saturated heterocycle having 4 to 5 carbon atoms, and q represents the numbers 0 or 1, R[2] represents phenyl which is unsubstituted or monosubstituted of polysubstituted by identical or different substituents selected from the group consisting of cyano, nitro, halogen, in each case straight-chain or branched alkyl or alkoxy having 1 to 6 carbon atoms in each case straight-chain or branched halogenoalkyl or halogenoalkoxy having 1 to 4 carbon atoms and 1 to 9 identical or different halogen atoms, and phenethenyl or phenethynyl, each of which is unsubstituted or monosubstituted or polysubstituted by identical or different substituents, the substituents in each case being the phenyl substituents already mentioned above; or the radical —$(CH_2)_n$—$Z_m$—$(CH_2)_p$—R[5], where R[5] represents aryl which has 6 to 10 carbon atoms and which is unsubstituted or monosubstituted or polysubstituted by identical or different substituents selected from the group consisting of cyano, nitro, halogen, $C_{1-4}$-alkyl, $C_{1-4}$-alkoxy, halogeno-$C_{1-4}$-alkyl and halogeno-$C_{1-4}$-alkoxy, Z represents oxygen or sulphur or represents the group >C=O and n, m and p independently of one another represent the numbers 0 or 1, and R[3] and R[6] represent hydrogen, straight-chain or branched alkyl having 1 to 6 carbon atoms, phenyl which is unsubstituted or monosubstituted to polysubstituted by identical or different substituents as defined hereinabove, or aralkyl which has 6 to 10 carbon atoms in the aryl moiety and 1 to 4 carbon atoms in the alkyl moiety and which is unsubstitute or monosubstituted to polysubstituted by identical or different substituents, the substituents being selected from the group consisting of cyano, nitro, halogen, $C_{1-4}$-alkyl, $C_{1-4}$-alkoxy, halogeno-$C_{1-4}$ and halogen-$C_{1-4}$-alkoxy, with the proviso that if X represents the radical OR[1] and simultaneously q represents O, R[2] can only represent ortho-substituted phenyl when the substituents are halogen, halogenomethyl having 1 to 3 identical or different halogen atoms or phenyl, phenethenyl or phenethynyl each of which is unsubstituted or monosubstituted to polysubstituted by identical or different substituents, with the proviso that R[2] represents substituted phenyl when q represents 1 and X simultaneously represents the radical OR[1], and with the exception of the compounds 5-[(3,4-dimethoxyphenyl-methyl]-4-methoxy-3-(4-methoxyphenyl)-5H-furan-2-one, 4-methoxy-3-(3,4,5-trimethoxyphenyl)-5H-furan-2-one, 3-(3-chlorophenyl)-4-methoxy-5H-furan-2-one, 3-(4-chlorophenyl)-4-methoxy-5H-furan-2-one, 3-(3-fluorophenyl)-4-methoxy-5H-furan-2-one, 3-(4-fluorophenyl)-4-methoxy-5H-furan-2-one, 4-methoxy-3-(3-methoxyphenyl)-5H-furan-2-one, 4-(4-bromophenyl)-4-methoxy-5H-furan-2-one, 3-(3,4-dichlorophenyl)-4-methoxy-5H-furan-2-one, 3-[1,1'-biphenyl]-4-yl-4-methoxy-5H-furan-2-one, 4-methoxy-3-(4-methylphenyl)-5H-furan-2-one and 4-methoxy-3-(4-methoxyphenyl)-5H-furan-2-one, 3-(2-chlorophenyl)-4-methoxy-5H-furan-2-one, 3-(2-fluorophenyl)-4-methoxy-5H-furan-2-one and 4-methoxy-3-(2-methoxyphenyl)-5H-furan-2-one.

2. A 5H-furan-2-one according to claim 1, in which X represents the radical

where
R[4] represents hydrogen, methyl, ethyl, n- or i-propyl, n-, i-, s- or t-butyl, allyl, 2-propenyl, 1-methallyl, methoxymethyl, ethoxymethyl, methyloxyethyl, ethoxyethyl, methylcarbonyl, ethylcarbonyl, n-propylcarbonyl or i-propylcarbonyl, and R[7] represents hydrogen, hydroxy, amino, formyl, methyl, ethyl, n- or i-propyl, n-, i-, s- or t-butyl, methoxy, ethoxy, n- or i-propoxy, n-, i-, s- or t-butoxy, alkylcarbonyl having 1 to 6 carbon atoms, or represents in each case straight-chain or branched alkoxyalkyl, cyanoalkyl, halogenoalkylcarbonyl, alkoxycarbonylalkyl, alkylamino, alkylcarbonyloxy or aminocarbonylalkyl having 1 to 4 carbon atoms in the individual alkyl moieties and where appropriate 1 to 9 identical or different halogen atoms, or represents alkynyl having 2 to 4 carbon atoms, or represents cycloalkyl having 3 to 6 carbon atoms, or represents phenylcarbonyl, phenylalkyl or phenylalkoxy having 1 to 4 carbon atoms in the straight-chain or branched alkyl part, each of which is unsubstituted or monosubstituted to trisubstituted by identical or different substituents as defined hereinbelow in the definition of $R^5$, or represents the radical $NR^8R^9$ in which $R^8$ and $R^9$ in each case independently of each other represent methyl, ethyl, n- or i-propyl, methylcarbonyl, ethylcarbonyl or n- or i-propylcarbonyl, or $R^4$ and $R^7$ together with the nitrogen atom to which they are bound represent a saturated nitroalkylene chain having 4 to 5 carbon atoms, q represent the numbers 0 or 1, $R^2$ represents phenyl which is unsubstituted or monosubstituted to trisubstituted by identical or different substituents selected from the group consisting of cyano, nitro, fluorine, chlorine, bromine, methyl, ethyl, n- or i-propyl, methoxy, ethoxy, n- or i-propoxy, in each case straight-chain or branched halogenoalkyl or halogenoalkoxy having 1 or 2 carbon atoms and 1 to 5 identical or different fluorine or chlorine atoms, and phenethenyl or phenethynyl each of which is unsubstituted or monosubstituted to trisubstituted by identical or different substituents as defined hereinabove, as well as the radical $-(CH_2)_n-Z_m-(CH_2)_p-R^5$ where $R^5$ represents phenyl which is unsubstituted or monosubstituted to trisubstituted by identical or different substituents selected from the group consisting of cyano, nitro, fluorine, chlorine, bromine, methyl, ethyl, n- or i-propyl, methoxy, ethoxy, n- or i-propoxy and in each case straight-chain or branched halogenoalkyl and halogenoalkoxy having 1 or 2 carbon atoms and 1 to 5 identical or different fluorine or chlorine atoms, Z represents oxygen or sulphur or represents the group $>C=O$, and n, m and p independently of one another represents the number 0 or 1, $R^3$ and $R^6$ represent hydrogen, methyl, ethyl, n- or i-propyl, n-, i-, s- or t-butyl, phenyl which is unsubstituted or monosubstituted to trisubstituted by identical or different substituents, as defined hereinbelow or benzyl or phenethyl each of which is unsubstituted or monosubstituted to trisubstituted by identical or different substituents, the substituents being selected from the group consisting of cyano, nitro, fluorine, chlorine, bromine, methyl, ethyl, n- or i-propyl, methoxy, ethoxy, n- or i-propoxy, and in each case straight-chain or branched halogenoalkyl and halogenoalkoxy having 1 or 2 carbon atoms and 1 to 5 identical or different fluorine or chlorine atoms.

3. A 5-H-furan-2-one according to claim 1, in which X represents the radical $OR^1$, $R^1$ represents straight-chain or branched alkyl having 1 to 4 carbon atoms, or represents in each case straight-chain or branched cyanoalkyl, alkoxyalkyl, alkylcarbonyl, halogenoalkylcarbonyl or alkoxycarbonylalkyl having 1 to 6 carbon atoms in the individual alkyl moieties and where appropriate 1 to 9 identical or different halogen atoms, $R^3$ and $R^6$ represent hydrogen, straight-chain or branched alkyl having 1 to 6 carbon atoms, phenyl which is unsubstituted or monosubstituted to polysubstituted by identical or different substituents, or aralkyl which has 6 to 10 carbon atoms in the aryl moiety and 1 to 4 carbon atoms in the alkyl moiety and which is unsubstituted or monosubstituted or polysubstituted by identical or different substituents, the substituents in both instances being selected from the group consisting of cyano, nitro, halogen, $C_{1-4}$-alkyl, $C_{1-4}$-alkoxy, halogeno-$C_{1-4}$-alkyl and halogeno-$C_{1-4}$-alkoxy, and $R^2$ represents phenyl which is mono-, di- or trisubstituted in the meta- or para-position by identical or different substituents selected from the group consisting of cyano, nitro, halogen, in each case straight-chain or branched alkyl or alkoxy having 1 to 6 carbon atoms, in each case straight-chain or branched halogenoalkyl or halogenoalkoxy having 1 to 4 carbon atoms and 1 to 9 identical or different halogen atoms, or phenethenyl or phenethynyl each of which is unsubstituted or monosubstituted to polysubstituted by identical or different substituents selected from the group consisting of cyano, nitro, halogen, in each case straight-chain or branched alkyl or alkoxy having 1 to 6, carbon atoms, and in each case straight-chain or branched halogenoalkyl or halogenoalkoxy having 1 to 4 carbon atoms and 1 to 9 identical or different halogen atoms, or the radical $-(CH_2)_n-Z_m-(CH_2)_p-R^5$, where $R^5$ represents aryl which has 6 to 10 carbon atoms and which is unsubstituted or monosubstituted to polysubstituted by identical or different substituents selected from the group consisting of cyano, nitro, halogen, in each case straight-chain or branched alkyl or alkoxy having 1 to 6 carbon atoms, and in each case straight-chain or branched halogenoalkyl or halogenoalkoxy having 1 to 4 carbon atoms and 1 to 9 identical or different halogen atoms, Z represents oxygen or sulphur, or represents the group $>C=O$, and n, m and p represent the numbers 0 or 1, and q represents the numbers 0 or 1, with the exception of the compounds 5-[(3,4-dimethoxyphenyl-methyl]-4-methoxy-3-(4-methoxyphenyl)-5H-furan-2-one, 4-methoxy-3-(3,4,5-trimethoxyphenyl)-5H-furan-2-one, 3-(3-chlorophenyl)-4-methoxy-5H-furan-2-one, 3-(4-chlorophenyl)-4-methoxy-5H-furan-2-one, 3-(3-fluorophenyl)-4-methoxy-5H-furan-2-one, 3-(4-fluorophenyl)-4-methoxy-5H-furan-2-one, 4-methoxy-3-(3-methoxyphenyl)-5H-furan-2-one, 4-(4-bromophenyl)-4-methoxy-5H-furan-2-one, 3-(3,4-dichlorophenyl)-4-methoxy-5H-furan-2-one, 3-[1,1'-biphenyl]-4-yl-4-methoxy-5H-furan-2-one, 4-methoxy-3-(4-methylphenyl)-5H-furan-2-one and 4-methoxy-3-(4-methoxyphenyl)-5H-furan-2-one.

4. A 5-H-furan-2-one according to claim 1, in which represents the radical $OR^1$, $R^1$ represents straight-chain or branched alkyl having 1 to 4 carbon atoms, or represents in each case straight-chain or branched cyanoalkyl, alkoxyalkyl, alkylcarbonyl, halogenoalkylcarbonyl or alkoxycarbonylalkyl having 1 to 6 carbon atoms in the individual alkyl moieties and where appropriate 1 to 9 identical or different halogen atoms, $R^3$ and $R^6$ represent hydrogen, straight-chain or branched alkyl having 1 to 6 carbon atoms, phenyl which is unsubstituted or monosubstituted to polysubstituted by identical or different substituents, or aralkyl which has 6 to 10 carbon atoms in the aryl moiety and 1 to 4 carbon atoms in the arlkyl moiety and which is unsubstituted or monosubstituted or polysubstituted by identical or different substituents, the substituents in both instances being selected from the group consisting of cyano, nitro, halogen, $C_{1-4}$-alkyl, $C_{1-4}$-alkoxy, halogeno-$C_{1-4}$-alkyl and halogeno-$C_{1-4}$-alkoxy, and $R^2$ represents phenyl which is monosubstituted in the ortho-position by a substituent selected from the group consisting of cyano, nitro, halogen, in each case straight-chain or branched alkyl or alkoxy having 1 to 6 carbon atoms, in each case straight-chain or branched halogenoalkyl or halogenoalkoxy having 1 to 4 carbon atoms and 1 to 9 identical or different halogen atoms, and phenethenyl or phenethenyl each of which is unsubstituted or monosubstituted to polysubstituted by identical or different substituents, selected from the group consisting of cyano, nitro, halogen, in each case straight-chain or branched alkyl or alkoxy having 1 to 6 carbon atoms, in each case straight-chain or branched halogenoalkyl or halogenoalkoxy having 1 to 4 carbon atoms and 1 to 9 identical or different halogen atoms, and the radical $-(CH_2)_n-Z_m-(CH_2)_p-R^5$, $R^5$ represents aryl which has 6 to 10 carbon atoms and which is unsubstituted or monosubstituted to polysubstituted by identical or different substituents selected from the group consisting of cyano, nitro, halogen, in each case straight-chain or branched alkyl or alkoxy having 1 to 6 carbon atoms, and in each case straight-chain or branched halogenoalkyl or halogenoalkoxy having 1 to 4 carbon atoms and 1 to 9 identical or different halogen atoms, Z represents oxygen or sulphur, or represents the group $>C=O$, and n, m and p represent the numbers 0 or 1 and q represents the number 1.

5. A 5-H furan-2-one according to claim 1, in which X represents the radical $OR^1$, $R^1$ represents straight-chain or branched alkyl having 1 to 4 carbon atoms, or represents in each case straight-chain or branched cyanoalkyl, alkoxyalkyl, alkylcarbonyl, halogenoalkylcarbonyl or alkoxycarbonylalkyl having 1 to 6 carbon atoms in the individual alkyl moieties and where appropriate 1 to 9 identical or different halogen atoms, $R^2$ represents phenyl which is monosubstituted in the ortho-position by a member selected from the group consisting of halogen, halogenomethyl having 1 to 3 identical or different halogen atoms, and phenyl, phenethenyl or phenethynyl, each of which is unsubstituted or monosubstituted to polysubstituted by identical or different substituents selected from the group consisting of cyano, nitro, halogen, in each case straight-chain or branched alkyl or alkoxy having 1 to 6 carbon atoms, and in each case straight-chain or branched halogenoalkyl or halogenoalkoxy having 1 to 4 carbon atoms and 1 to 9 identical or different halogen atoms, and q represents the number 0, with the exception of the compounds 3-(2-chlorophenyl)-4-methoxy-5H-furan-2-one, 3-(2-fluorophenyl)-4-methoxy-5H-furan-2-one and 4-methoxy-3-(2-methoxyphenyl)-5H-furan-2-one.

6. A 5H-furan-2-one according to claim 1, in which

X represents the radical $OR^1$ $R^1$ represents methyl, ethyl, n- or i-propyl or n-, i-, s- or t-butyl, or represents in each case straight-chain or branched cyanoalkyl, alkoxyalkyl or alkoxycarbonylalkyl having 1 to 4 carbon atoms in the individual alkyl moieties, $R^3$ and $R^6$ represent hydrogen, methyl, ethyl, n- or i-propyl, n-, i-, s- or t-butyl, phenyl which are unsubstituted or monosubstituted to trisubstituted by identical or different substituents, or benzyl or phenethyl, each of which is unsubstituted or monosubstituted to trisubstituted by identical or different substituents, the substituents in each case being selected from the group consisting of cyano, nitro, fluorine, chlorine, bromine, methyl, ethyl, n- or i-propyl, methoxy, ethoxy, n- or i-propoxy, and in each case straight-chain halogen or halogenozlkoxy having 1 or 2 carbon atoms and 1 to 5 identical or different fluorine or chlorine atoms;

$R^2$ represents phenyl which is monosubstituted, di- or trisubstituted in the meta- or para-position by identical or different substituents selected from the group consisting of cyano, nitro, fluorine, chlorine, bromine, methyl, ethyl, n- or i-propyl, methoxy, ethoxy, n- or i-propoxy, in each case straight-chain or branched halogenoalkyl or halogenoalkoxy having 1 to 2 carbon atoms and 1 to 5 identical or different fluorine or chlorine atoms, and phenylethenyl or phenethynyl, each of which is unsubstituted or monosubstituted to trisubstituted by identical or different substituents selected from the group consisting of cyano, nitro, fluorine, chlorine, bromine, methyl, ethyl, n- or i-propyl, methoxy, ethoxy, n- or i-propoxy, in each case straight-chain or branched halogenoalkyl or halogenoalkoxy having 1 or 2 carbon atoms and 1 to 5 identical or different fluorine or chlorine atoms, and the radical $-(CH_2)_n-Z_m-(CH_2)_p-R^5$, where $R^5$ represents phenyl which is unsubstituted or monosubstituted to trisubstituted by identical or different substituents selected from the group consisting of cyano, nitro, fluorine, chlorine, bromine, methyl, ethyl, n- or i-propyl, methoxy, ethoxy, n- or i-propoxy and in each case straight-chain or branched halogenoalkyl or halogenoalkoxy having 1 or 2 carbon atoms and 1 to 5 identical or different fluorine or chlorine atoms;

Z represents oxygen or sulphur, or represents the group $>C=O$ and n, m and p represent the numbers 0 or 1 and q represents the numbers 0 or 1, with the exception of the compounds 5-[(3,4-dimethoxyphenyl-methyl]-4-methoxy-3-(4-methoxyphenyl)-5H-furan-2-one, 4-methoxy-3-(3,4,5-trimethoxyphenyl)-5H-furan-2-one, 3-(3-chlorophenyl)-4-methoxy-5H-furan-2-one, 3-(4-chlorophenyl)-4-methoxy-5H-furan-2-one, 4-methoxy-3-(3-methoxyphenyl)-5H-furan-2-one, 4-(4-bromophenyl)-4-methoxy-5H-furan-2-one, 3-(3,4-dichlorophenyl)-4-methoxy-5H-furan-2-one, 3-[1,1'-biphenyl]-4-yl-4-methoxy-5H-furan-2-one, 4-methoxy-3-(4-methylphenyl)-5H-furan-2-one and 4-methoxy-3-(4-methoxy-3-(4-methoxyphenyl)-5H-furan-2-one.

7. A 5H-furan-2-one according to claim 1, in which

X represents the radical $OR^1$ $R^1$ represents methyl, ethyl, n- or i-propyl or n-, i-, s- or t-butyl, or represents in each case straight-chain or branched cyanoalkyl, alkoxyalkyl or alkoxycarbonylalkyl having 1 to 4 carbon atoms in the individual alkyl moieties, $R^3$ and $R^6$ represent hydrogen, methyl, ethyl, n- or i-propyl, n-, i-, s- or t-butyl, phenyl which are unsubstituted or monosubstituted to trisubstituted by identical or different substituents, or benzyl or phenethyl, each of which is unsubstituted or monosubstituted to trisubstituted by identical or different substituents, the substituents in each case being selected from the group consisting of cyano, nitro, fluorine, chlorine, bromine, methyl, ethyl, n- or i-propyl, methoxy, ethoxy, n- or i-propoxy, and in each case straight-chain halogen or halogenoalkoxy having 1 or 2 carbon atoms and 1 to 5 identical or different fluorine or chlorine atoms;

$R^2$ represents phenyl which is monosubstituted in the ortho-position by a substituent selected from the group consisting of cyano, nitro, fluorine, chlorine, bromine, methyl, ethyl, n- or i-propyl, methoxy, ethoxy, n- or i-propoxy, in each case straight-chain or branched halogenoalkyl or halogenoalkoxy having 1 or 2 carbon atoms and 1 to 5 identical or different fluorine or chlorine atoms, and phenethenyl or phenethynyl, each of which is unsubstituted or monosubstituted to trisubstituted by identical or different substituents selected from the group consisting of cyano, nitro, fluorine, chlorine, bromine, methyl, ethyl, n- or i-propyl, methoxy, ethoxy, n- or i-propoxy, in each case straight-chain or branched halogenoalkyl or halogenoalkoxy having 1 or 2 carbon atoms and 1 to 5 identical or different fluorine or chlorine atoms, and the radical $-(CH_2)_n-Z_m-(CH_2)_p-R^5$ where $R^5$ represents phenyl which is unsubstituted or monosubstituted to polysubstituted by identical or different substituents selected from the group consisting of cyano, nitro, fluorine, chlorine, bromine, methyl, ethyl, n- or i-propyl, methoxy, ethoxy, n- or i-propoxy, and in each case straight-chain or branched halogenoalkyl or halogenoalkoxy having 1 or 2 carbon atoms and 1 to 5 identical or different fluorine or chlorine atoms;

Z represents oxygen or sulphur or represents the group $>C=O$ and n, m and p represent the numbers 0 or 1, and q represents the number 1.

8. A 5H-furan-2-one according to claim 1, in which X represents the radical $OR^1$ $R^1$ represents methyl, ethyl, n- or i-propyl or n-, i-, s- or t-butyl, or represents in each case straight-chain or branched cyanoalkyl, alkoxyalkyl or alkoxycarbonylalkyl having 1 to 4 carbon atoms in the individual alkyl moieties, $R^3$ and $R^6$ represent hydrogen, methyl, ethyl, n- or i-propyl, n-, i-, s- or t-butyl, phenyl which are unsubstituted or monosubstituted to trisubstituted by identical or different substituents, or benzyl or phenethyl, each of which is unsubstituted or monosubstituted to trisubstituted by identical or different substituents, the substituents in each case being selected from the group consisting of cyano, nitro, fluorine, chlorine, bromine, methyl, ethyl, n- or i-propyl, methoxy, ethoxy, n- or i-propoxy, and in each case straight-chain halogen or halogenoalkoxy having 1 or 2 carbon atoms and 1 to 5 identical or different fluorine or chlorine atoms;

$R^2$ represents phenyl which is monosubstituted in the ortho-position by a member selected from the group consisting of fluorine, chlorine, bromine, halogenomethyl having 1 to 3 identical or different fluorine or chlorine atoms, and phenyl, phenethenyl or phenethynyl each of which is unsubstituted or monosubstituted to trisubstituted by identical or different substituents selected from the group consisting of cyano, nitro, fluorine, chlorine, bromine, methyl, ethyl, n- or i-propyl, methoxy, ethoxy, n- or i-propoxy, and in each case straight-chain or branched halogenoalkyl or halogenoalkoxy having 1 or 2 carbon atoms and 1 to 5 identical or different fluorine or chlorine atoms, and q represents the number 0, with the exception of the compounds 3-(2-chlorophenyl)-4-methoxy-5H-furan-2-one, 3-(2-fluorophenyl)-4-methoxy-5H-furan-2-one, 4-methoxy-3-(2-methoxyphenyl)-5H-furan-2-one.

9. A 5H-furan-2-one according to claim 1, in which X represents the radical

where $R^4$ represents hydrogen, methyl, ethyl or n- or i-propyl, methylcarbonyl or ethylcarbonyl, and $R^7$ represents hydrogen, hydroxy, amino, formyl, methyl, ethyl, n- or i-propyl, n-, i-, s- or t-butyl, methoxy, ethoxy, n- or i-propoxy, n-, i-, s- or t-butoxy, methoxymethyl, ethoxymethyl, methoxyethyl, ethoxyethyl, cyanomethyl, cyanoethyl, methylcarbonyl, ethylcarbonyl, n- or i-propylcarbonyl, n-, i-, s- or t-butylcarbonyl, halogenoalkylcarbonyl having 1 or 2 carbon atoms and 1 to 5 identical or different fluoro- or chloro atoms, methoxycarbonylmethyl, ethoxycarbonylmethyl, methoxycarbonylethyl, ethoxycarbonylethyl, methylamino, ethylamino, n- or i-propylamino, methylcarbonyloxy, ethylcarbonyloxy, n- or i-propylcarbonyloxy, aminocarbonylmethyl, cyclopropyl, cyclopentyl, cyclohexyl, phenylcarbonyl, phenylalkyl, and phenylalkyloxy in each case having 1 or 2 carbon atoms in the individual alkyl part, or represents the radical $NR^8R^9$, in which $R^8$ and $R^9$ independently of each other represent in each case methyl, ethyl or methylcarbonyl, or $R^4$ and $R^7$ together with the nitrogen atom, to which they are bond represent a saturated heteroalkylene chain having 4 to 5 carbon atoms, q represent the number 0 or 1, $R^2$ represents phenyl which is unsubstituted or monosubstituted to trisubstituted by identical or different substituents, at least one of the substituents being in the meta-position and being selected from the group consisting of trifluoromethyl, trifluoromethoxy, fluorine, chlorine and bromine, the ortho- and para-positions optionally being substituted by fluorine, chlorine, bromine, methyl, ethyl, n- or i-propyl, or the radical $-(CH_2l)_n-Z_m-(CH_2l)_p-R^5$, where $R^5$ represents phenyl which is unsubstituted or monosubstituted to trisubstituted by identical or different substituents selected from the group consisting of fluorine, chlorine, bromine, trifluoromethyl, trifluoromethoxy, methyl, ethyl and n- or i-propyl, Z represents oxygen or sulphur or represents the group >C=O, n, m and p represent the numbers 0 or 1, and $R^3$ and $R^6$ represent hydrogen, methyl, ethyl, n- or i-propyl, n-, i-, s- or t-butyl, or phenyl or benzyl each of which is unsubstituted or monosubstituted or disubstituted by identical or different substituents selected from the group consisting of fluorine, chlorine, bromine, methyl, ethyl, n- or i-propyl, trifluoromethyl and trifluoromethoxy.

10. A compound according to claim 1, wherein such compound is 4-methoxy-3-(2-methylphenyl)-5H-furan-2-one of the formula

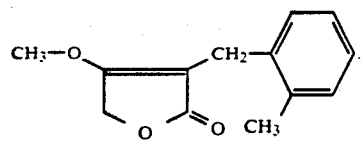

11. A compound according to claim 1, wherein such compound is 4-methylcarbonylamino-3-(3-trifluoromethylphenyl)-5H-furan-2-one of the formula

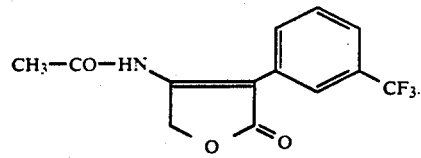

12. A herbicidal composition comprising a herbicidally effective amount of a 5H-furan-2-one compound according to claim 1 and an inert carrier.

13. A method for combatting undesired vegetation which comprises applying to such vegetation, or to a locus from which it is desired to exclude such vegetation, a herbicidally effective amount of 5H-furan-2-one according to claim 1.

14. The method according to claim 13, wherein such compound is
4-methoxy-3-(2-methylphenyl)-5H-furan-2-one or
4-methylcarbonylamino-3-(3-trifluoromethylphenyl)-5H-furan-2-one.

* * * * *

UNITED STATES PATENT AND TRADEMARK OFFICE
CERTIFICATE OF CORRECTION

PATENT NO. : 5,094,681

DATED : March 10, 1992

INVENTOR(S) : Kramer et al.

It is certified that error appears in the above-identified patent and that said Letters Patent is hereby corrected as shown below:

| | |
|---|---|
| Col. 45, line 61 | Delete " $C_{104}$-alkyl " and substitute $C_{1-4}$-alkyl -- |
| Col. 48, line 25 | Delete " $-(CH_2 1)_n-Z_m-(CH_2 1-$ " and substitute -- $-(CH_2)_n-Z_m-(CH_2-$ -- |
| Col. 48, line 56 | Before " represents " insert -- X -- |
| Col. 49, line 1 | Delete " arlkyl " and substitute -- alkyl -- |
| Col. 49, line 16 | Delete " phenethenyl " (second occurrence) and substitute -- phenethynyl -- |
| Col. 49, line 26 | Delete " $-(CH_2 1)_n$ " and substitute -- $-(CH_2)_n$ -- |
| Col. 50, lines 17-18 | Delete " halogenozlkoxy " and substitute -- halogenoalkoxy -- |
| Col. 50, line 27 | Delete 1 to 2 " and substitute -- 1 or 2 -- |
| Col. 50, line 59 | After " methoxy-5H-furan-2-one, "insert -- 3-(3-fluorophenyl)-4-methoxy-5H-furan-2-one, 3-(4-fluorophenyl-4-methoxy-5H-furan-2-one, -- |

UNITED STATES PATENT AND TRADEMARK OFFICE
CERTIFICATE OF CORRECTION

PATENT NO. : 5,094,681
DATED : March 10, 1992
INVENTOR(S) : Kramer et al.

It is certified that error appears in the above-indentified patent and that said Letters Patent is hereby corrected as shown below:

Col. 52, line 63  Delete " $-(CH_21)_n-Z_m-(CH_21-$ " and substitute -- $-(CH_2)_n-Z_m-(CH_2-$ --

Signed and Sealed this

Fifteenth Day of February, 1994

Attest:

BRUCE LEHMAN

Attesting Officer

Commissioner of Patents and Trademarks